(12) United States Patent
Bhimavarapu

(10) Patent No.: US 12,718,938 B2
(45) Date of Patent: Aug. 25, 2026

(54) PATIENT SUPPORT SYSTEMS AND METHODS FOR ASSISTING CAREGIVERS WITH PATIENT CARE

(71) Applicant: Stryker Corporation, Kalamazoo, MI (US)

(72) Inventor: Krishna S. Bhimavarapu, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 18/374,014

(22) Filed: Sep. 28, 2023

(65) Prior Publication Data

US 2024/0021304 A1 Jan. 18, 2024

Related U.S. Application Data

(63) Continuation of application No. 16/020,085, filed on Jun. 27, 2018, now Pat. No. 11,810,667.

(Continued)

(51) Int. Cl.
*G16H 40/63* (2018.01)
*A61G 7/00* (2006.01)

(Continued)

(52) U.S. Cl.
CPC ............. *G16H 40/63* (2018.01); *A61G 7/001* (2013.01); *A61G 7/012* (2013.01); *A61G 7/015* (2013.01);

(Continued)

(58) Field of Classification Search
CPC ........ A61G 7/001; A61G 7/012; A61G 7/015; A61G 7/018; A61G 7/0509; A61G 7/0514;

(Continued)

(56) References Cited

U.S. PATENT DOCUMENTS 5,113,214 A 5/1992 Nagata et al.
5,276,432 A 1/1994 Travis (Continued)

FOREIGN PATENT DOCUMENTS

CN 101789230 A 7/2010
DE 19505162 C1 3/1996

(Continued)

OTHER PUBLICATIONS

Apple, "Adjust the Brightness on you iPhone, IPad, or IPod Touch", https://support.apple.com/en-us/HT202613, 2018, 2 pages.

(Continued)

*Primary Examiner* — Shahid Merchant
*Assistant Examiner* — Hunter J Rasnic
(74) *Attorney, Agent, or Firm* — Howard & Howard Attorneys PLLC

(57) ABSTRACT

A patient support system for providing improved guidance and/or troubleshooting with respect to a patient support apparatus. A user interface is configured to receive inputs from a user, and an information output device is configured to provide instructions to the user. A controller determines a guidance protocol for the user based on the inputs. The guidance protocol comprises user-performed actions to be performed by the user in response to the instructions provided to the user with the information output device. The guidance protocol may be initiated and/or determined based on a troubleshooting request and/or an uncorrelated sequence of user inputs. At least one of the user-performed actions may be configured to control operational functions of a patient support apparatus. Methods for improving patient care by providing the guidance and/or troubleshooting are also disclosed.

19 Claims, 15 Drawing Sheets

Related U.S. Application Data

(60) Provisional application No. 62/525,363, filed on Jun. 27, 2017.

(51) Int. Cl.

| | |
|---|---|
| ***A61G 7/012*** | (2006.01) |
| ***A61G 7/015*** | (2006.01) |
| ***A61G 7/018*** | (2006.01) |
| ***A61G 7/05*** | (2006.01) |
| ***A61G 7/057*** | (2006.01) |
| ***G06F 3/0488*** | (2022.01) |
| ***G06F 9/451*** | (2018.01) |
| ***G16H 40/60*** | (2018.01) |
| ***G16H 40/67*** | (2018.01) |
| ***G16H 50/20*** | (2018.01) |
| ***G16H 50/30*** | (2018.01) |
| ***G16H 70/20*** | (2018.01) |

(52) U.S. Cl.

CPC .......... *A61G 7/018* (2013.01); *A61G 7/0509* (2016.11); *A61G 7/0514* (2016.11); *A61G 7/0524* (2016.11); *A61G 7/05769* (2013.01); *A61G 7/05792* (2016.11); *G06F 3/0488* (2013.01); *G06F 9/453* (2018.02); *G16H 40/60* (2018.01); *G16H 40/67* (2018.01); *G16H 50/20* (2018.01); *G16H 50/30* (2018.01); *G16H 70/20* (2018.01); *A61G 2203/12* (2013.01); *A61G 2203/16* (2013.01); *A61G 2203/20* (2013.01); *A61G 2203/36* (2013.01); *A61G 2203/40* (2013.01); *A61G 2210/90* (2013.01)

(58) Field of Classification Search

CPC ........... A61G 7/05792; A61G 7/05769; A61G 2203/12; A61G 2203/16; A61G 2203/02; A61G 2203/36; A61G 2203/40; A61G 2210/90; G06F 3/0488; G06F 9/453; G16H 40/60; G16H 40/63; G16H 40/67; G16H 50/20; G16H 50/30; G16H 70/20; A61B 5/742

See application file for complete search history.

(56) References Cited

U.S. PATENT DOCUMENTS

| | | | |
|---|---|---|---|
| 5,434,621 | A | 7/1995 | Yu |
| 5,640,953 | A | 6/1997 | Bishop et al. |
| 5,645,667 | A | 7/1997 | Kusen |
| 5,664,270 | A | 9/1997 | Bell et al. |
| 5,715,548 | A | 2/1998 | Weismiller et al. |
| 5,971,913 | A | 10/1999 | Newkirk et al. |
| 6,320,510 | B2 | 11/2001 | Menkedick et al. |
| 6,340,977 | B1 | 1/2002 | Lui et al. |
| 6,362,725 | B1 | 3/2002 | Ulrich et al. |
| 6,702,314 | B1 | 3/2004 | Crose |
| 6,876,303 | B2 | 4/2005 | Reeder et al. |
| 6,948,592 | B2 | 9/2005 | Kavounas |
| 7,154,397 | B2 | 12/2006 | Zerhusen et al. |
| 7,296,312 | B2 | 11/2007 | Menkedick et al. |
| 7,319,386 | B2 | 1/2008 | Collins, Jr. et al. |
| 7,336,187 | B2 | 2/2008 | Hubbard, Jr. et al. |
| 7,389,552 | B1 | 6/2008 | Reed et al. |
| 7,443,302 | B2 | 10/2008 | Reeder et al. |
| 7,472,439 | B2 | 1/2009 | Lemire et al. |
| 7,487,562 | B2 | 2/2009 | Frondorf et al. |
| 7,490,021 | B2 | 2/2009 | Holland et al. |
| 7,570,152 | B2 | 8/2009 | Smith et al. |
| 7,690,059 | B2 | 4/2010 | Lemire et al. |
| 7,747,644 | B1 | 6/2010 | Reihl et al. |
| 7,888,901 | B2 | 2/2011 | Larson et al. |
| 7,895,519 | B1 | 2/2011 | Allegrezza et al. |
| 8,069,157 | B2 | 11/2011 | Jam |
| 8,117,701 | B2 | 2/2012 | Bobey et al. |
| 8,121,856 | B2 | 2/2012 | Huster et al. |
| 8,143,846 | B2 | 3/2012 | Herman et al. |
| 8,165,908 | B2 | 4/2012 | Bolle et al. |
| 8,209,608 | B1 | 6/2012 | Linyard et al. |
| 8,266,742 | B2 | 9/2012 | Andrienko |
| 8,308,237 | B2 | 11/2012 | Kunou |
| 8,319,633 | B2 | 11/2012 | Becker et al. |
| 8,334,779 | B2 | 12/2012 | Zerhusen et al. |
| 8,341,777 | B2 | 1/2013 | Hensley et al. |
| 8,344,860 | B2 | 1/2013 | Collins, Jr. et al. |
| 8,410,943 | B2 | 4/2013 | Metz et al. |
| 8,413,270 | B2 | 4/2013 | Turner et al. |
| 8,413,271 | B2 | 4/2013 | Blanchard et al. |
| 8,432,287 | B2 | 4/2013 | O'Keefe et al. |
| 8,442,738 | B2 | 5/2013 | Patmore |
| 8,464,380 | B2 | 6/2013 | Bobey et al. |
| 8,525,682 | B2 | 9/2013 | Dixon et al. |
| 8,544,126 | B2 | 10/2013 | Elliott et al. |
| 8,552,880 | B2 | 10/2013 | Kopp et al. |
| 8,604,917 | B2 | 12/2013 | Collins et al. |
| 8,641,301 | B2 | 2/2014 | Yang et al. |
| 8,650,682 | B2 | 2/2014 | Herman |
| 8,674,839 | B2 | 3/2014 | Zerhusen et al. |
| 8,716,941 | B2 | 5/2014 | Kim |
| 8,756,078 | B2 | 6/2014 | Collins, Jr. et al. |
| 8,768,520 | B2 | 7/2014 | Oexman et al. |
| 8,789,102 | B2 | 7/2014 | Pickelsimer et al. |
| 8,847,756 | B2 | 9/2014 | Tallent et al. |
| 8,868,542 | B2 | 10/2014 | Kimball et al. |
| 8,870,812 | B2 | 10/2014 | Alberti et al. |
| 8,896,524 | B2 | 11/2014 | Birnbaum et al. |
| 8,923,994 | B2 | 12/2014 | Laikari et al. |
| 8,924,218 | B2 | 12/2014 | Corpier et al. |
| 8,926,535 | B2 | 1/2015 | Rawls-Meehan |
| 8,984,685 | B2 | 3/2015 | Robertson et al. |
| 9,001,038 | B2 | 4/2015 | Kasahara |
| 9,032,510 | B2 | 5/2015 | Sampathkumaran et al. |
| 9,038,217 | B2 | 5/2015 | Elliot et al. |
| 9,088,282 | B2 | 7/2015 | Holenarsipur et al. |
| 9,126,571 | B2 | 9/2015 | Lemire et al. |
| 9,138,173 | B2 | 9/2015 | Penninger et al. |
| 9,173,792 | B2 | 11/2015 | Goffer |
| 9,204,823 | B2 | 12/2015 | Derenne et al. |
| 9,220,650 | B2 | 12/2015 | Bobey et al. |
| 9,228,885 | B2 | 1/2016 | Zerhusen et al. |
| 9,230,421 | B2 | 1/2016 | Reeder et al. |
| 9,233,033 | B2 | 1/2016 | Valentino et al. |
| 9,259,369 | B2 | 2/2016 | Derenne et al. |
| 9,262,876 | B2 | 2/2016 | Wood et al. |
| 9,298,884 | B1 | 3/2016 | Ahmad |
| 9,320,664 | B2 | 4/2016 | Newkirk et al. |
| 9,342,677 | B2 | 5/2016 | Ali et al. |
| 9,381,125 | B2 | 7/2016 | Herbst et al. |
| 9,424,699 | B2 | 8/2016 | Kusens et al. |
| 9,456,938 | B2 | 10/2016 | Blickensderfer et al. |
| 9,463,126 | B2 | 10/2016 | Zerhusen et al. |
| 9,466,163 | B2 | 10/2016 | Kusens et al. |
| 9,486,084 | B2 | 11/2016 | Connell et al. |
| 9,569,591 | B2 | 2/2017 | Vanderpohl, III |
| 9,593,833 | B2 | 3/2017 | McMannon et al. |
| 9,655,798 | B2 | 5/2017 | Zerhusen et al. |
| 9,691,206 | B2 | 6/2017 | Kusens et al. |
| 9,774,991 | B2 | 9/2017 | Kusens |
| 9,814,410 | B2 | 11/2017 | Kostic et al. |
| 9,838,849 | B2 | 12/2017 | Kusens |
| 9,844,275 | B2 | 12/2017 | Nunn et al. |
| 9,849,051 | B2 | 12/2017 | Newkirk et al. |
| 9,858,741 | B2 | 1/2018 | Kusens et al. |
| 9,892,310 | B2 | 2/2018 | Kusens et al. |
| 9,892,311 | B2 | 2/2018 | Kusens et al. |
| 9,916,649 | B1 | 3/2018 | Kusens |
| 9,934,427 | B2 | 4/2018 | Derenne et al. |
| 9,940,810 | B2 | 4/2018 | Derenne et al. |
| 9,984,521 | B1 | 5/2018 | Kusens et al. |
| 9,998,857 | B2 | 6/2018 | Kusens |
| 9,999,555 | B2 | 6/2018 | Magill et al. |
| 10,004,654 | B2 | 6/2018 | Zerhusen et al. |

(56) References Cited

U.S. PATENT DOCUMENTS 10,034,979 B2 7/2018 Bechtel et al.
10,052,249 B2 8/2018 Elliott et al.
10,098,796 B2 10/2018 Valentino et al.
10,136,841 B2 11/2018 Alghazi
10,172,752 B2 1/2019 Goffer
10,188,569 B2 1/2019 Elku et al.
10,251,797 B2* 4/2019 Kramer ................ A61G 7/0528
10,811,136 B2 10/2020 Bhimavarapu et al.
11,096,850 B2 8/2021 Bhimavarapu et al.
11,202,729 B2 12/2021 Desaulniers
11,337,872 B2 5/2022 Bhimavarapu et al.
11,382,812 B2 7/2022 Bhimavarapu et al.
2002/0014951 A1 2/2002 Kramer et al.
2002/0059679 A1 5/2002 Weismiller et al.
2003/0183427 A1 10/2003 Tojo et al.
2004/0083394 A1 4/2004 Brebner et al.
2005/0114140 A1 5/2005 Brackett et al.
2006/0077186 A1 4/2006 Park et al.
2006/0102392 A1 5/2006 Johnson et al.
2006/0150332 A1 7/2006 Weismiller et al.
2006/0277683 A1 12/2006 Lamire et al.
2007/0066866 A1* 3/2007 Noguchi ................ A61B 1/015
600/101
2007/0130692 A1 6/2007 Lemire et al.
2007/0157385 A1* 7/2007 Lemire ................ A61G 7/0524
5/618
2007/0163045 A1* 7/2007 Becker ................... A61G 7/015
5/616
2007/0180616 A1 8/2007 Newkirk et al.
2007/0210917 A1* 9/2007 Collins .................. G08B 5/222
340/539.1
2007/0219950 A1 9/2007 Crawford
2008/0141459 A1 6/2008 Hamberg et al.
2008/0172789 A1 7/2008 Elliot et al.
2008/0235871 A1 10/2008 York
2008/0235872 A1* 10/2008 Newkirk ............... G06F 3/0481
5/658
2009/0049610 A1 2/2009 Heimbrock et al.
2009/0153370 A1 6/2009 Cooper et al.
2010/0039414 A1 2/2010 Bell
2010/0212087 A1 8/2010 Leib et al.
2011/0080421 A1 4/2011 Capener
2011/0144548 A1 6/2011 Elliott et al.
2011/0162067 A1 6/2011 Shuart et al.
2011/0169653 A1 7/2011 Wang et al.
2011/0205061 A1 8/2011 Wilson et al.
2012/0023670 A1 2/2012 Zerhusen et al.
2012/0089419 A1* 4/2012 Huster ................... A61G 7/015
705/3
2012/0137436 A1 6/2012 Andrienko
2012/0215360 A1 8/2012 Zerhusen et al.
2012/0239173 A1 9/2012 Laikari et al.
2012/0239420 A1 9/2012 Stapelfeldt et al.
2013/0138452 A1 5/2013 Cork et al.
2013/0142367 A1 6/2013 Berry et al.
2013/0227787 A1 9/2013 Herbst et al.
2013/0238991 A1 9/2013 Jung et al.
2013/0300867 A1 11/2013 Yoder
2013/0318716 A1* 12/2013 Vanderpohl, III ........ G06F 3/14
5/600
2013/0340169 A1* 12/2013 Zerhusen ............... A61G 7/053
177/144
2014/0076644 A1 3/2014 Derenne et al.
2014/0237721 A1 8/2014 Lemire et al.
2014/0259410 A1 9/2014 Zerhusen et al.
2014/0259414 A1* 9/2014 Hayes .................. A61B 5/7275
600/595
2014/0265181 A1 9/2014 Lambarth et al.
2014/0297327 A1 10/2014 Heil et al.
2014/0313700 A1 10/2014 Connell et al.
2014/0342330 A1 11/2014 Freeman et al.
2014/0343968 A1* 11/2014 Wilson ................... G16H 10/60
705/3
2015/0002393 A1 1/2015 Cohen et al.
2015/0033295 A1 1/2015 Huster
2015/0060162 A1 3/2015 Goffer
2015/0070319 A1 3/2015 Pryor
2015/0077502 A1* 3/2015 Jordan ................ G06F 3/04883
348/14.03
2015/0077534 A1 3/2015 Derenne et al.
2015/0109442 A1 4/2015 Derenne et al.
2015/0154002 A1 6/2015 Weinstein et al.
2015/0182400 A1* 7/2015 Meyer ................ A61G 7/05776
5/710
2015/0250669 A1 9/2015 Elliott et al.
2015/0317068 A1 11/2015 Marka et al.
2016/0012218 A1 1/2016 Perna et al.
2016/0022039 A1 1/2016 Paul et al.
2016/0038361 A1 2/2016 Bhimavarapu et al.
2016/0045382 A1 2/2016 Goffer
2016/0049028 A1 2/2016 Kusens et al.
2016/0050217 A1 2/2016 Mare et al.
2016/0055299 A1* 2/2016 Yarnell .................. G16H 10/60
705/2
2016/0063897 A1* 3/2016 Rusin ....................... G09B 5/02
434/262
2016/0065909 A1 3/2016 Derenne et al.
2016/0095774 A1 4/2016 Bobey et al.
2016/0140307 A1 5/2016 Brosnan et al.
2016/0180668 A1 6/2016 Kusens et al.
2016/0183864 A1 6/2016 Kusens et al.
2016/0188815 A1* 6/2016 Kudo ................... G06F 3/0481
705/2
2016/0193095 A1 7/2016 Roussy et al.
2016/0199240 A1* 7/2016 Newkirk ................ A61G 7/018
715/771
2016/0213537 A1 7/2016 Hayes et al.
2016/0224195 A1 8/2016 Okabe et al.
2016/0247342 A1 8/2016 Kusens et al.
2016/0296396 A1 10/2016 Kolar et al.
2016/0324705 A1 11/2016 Bach Castillo
2016/0338891 A1 11/2016 Agdeppa et al.
2016/0366327 A1 12/2016 Kusens
2016/0367420 A1 12/2016 Zerhusen et al.
2016/0371786 A1 12/2016 Kusens et al.
2017/0027787 A1 2/2017 Huster et al.
2017/0027789 A1 2/2017 St.John et al.
2017/0035631 A1 2/2017 Tsusaka et al.
2017/0049642 A9 2/2017 Valentino et al.
2017/0055113 A1 2/2017 Kusens
2017/0076526 A1 3/2017 Kusens et al.
2017/0094477 A1 3/2017 Kusens et al.
2017/0097800 A1 4/2017 Vanderpohl, III
2017/0098048 A1 4/2017 Brosnan et al.
2017/0109770 A1 4/2017 Kusens et al.
2017/0111770 A1 4/2017 Kusens
2017/0116790 A1 4/2017 Kusens et al.
2017/0124844 A1 5/2017 Huster et al.
2017/0128296 A1 5/2017 Kostic et al.
2017/0143565 A1 5/2017 Childs et al.
2017/0172827 A1* 6/2017 Schaaf .................. A61G 5/006
2017/0193177 A1 7/2017 Kusens
2017/0193180 A1 7/2017 Kusens et al.
2017/0193279 A1 7/2017 Kusens et al.
2017/0193772 A1 7/2017 Kusens et al.
2017/0195637 A1 7/2017 Kusens et al.
2017/0213445 A1 7/2017 Kusens
2017/0224562 A1 8/2017 Zerhusen et al.
2017/0229009 A1 8/2017 Foster et al.
2017/0259811 A1 9/2017 Coulter et al.
2017/0281440 A1 10/2017 Puvogel et al.
2017/0352212 A1 12/2017 Kusens et al.
2017/0357320 A1* 12/2017 Chaudhri ............. G06F 3/0412
2017/0364644 A1 12/2017 Johnson et al.
2018/0017945 A1 1/2018 Sidhu et al.
2018/0039743 A1 2/2018 Dixon et al.
2018/0040091 A1 2/2018 Kusens
2018/0041864 A1 2/2018 Kusens
2018/0055418 A1 3/2018 Kostic et al.
2018/0056985 A1 3/2018 Coulter et al.
2018/0084390 A1 3/2018 Kusens
2018/0096550 A1 4/2018 Kusens et al.
2018/0110445 A1 4/2018 Bhimavarapu et al.

(56) References Cited

U.S. PATENT DOCUMENTS

| | | | |
|---|---|---|---|
| 2018/0114053 | A1 | 4/2018 | Kusens et al. |
| 2018/0137340 | A1 | 5/2018 | Kusens et al. |
| 2018/0151010 | A1 | 5/2018 | Kusens et al. |
| 2018/0161225 | A1 | 6/2018 | Zerhusen et al. |
| 2018/0167816 | A1 | 6/2018 | Kusens et al. |
| 2018/0184984 | A1 | 7/2018 | Zerhusen et al. |
| 2018/0189946 | A1 | 7/2018 | Kusens et al. |
| 2018/0211464 | A1 | 7/2018 | Kusens et al. |
| 2018/0218489 | A1 | 8/2018 | Kusens |
| 2018/0250177 | A1 | 9/2018 | Magill et al. |
| 2018/0271286 | A1 | 9/2018 | Jacobs et al. |
| 2018/0271287 | A1 | 9/2018 | Jacobs et al. |
| 2018/0303687 | A1 | 10/2018 | Moreno et al. |
| 2018/0369035 | A1 | 12/2018 | Bhimavarapu et al. |
| 2018/0369037 | A1 | 12/2018 | Desaulniers et al. |
| 2018/0369038 | A1 | 12/2018 | Bhimavarapu et al. |
| 2018/0369039 | A1 | 12/2018 | Bhimavarapu et al. |
| 2018/0374573 | A1 | 12/2018 | Bhimavarapu et al. |
| 2018/0374577 | A1 | 12/2018 | Bhimavarapu |
| 2019/0008708 | A1 | 1/2019 | Moreno et al. |
| 2019/0024882 | A1 | 1/2019 | Jonsson et al. |
| 2019/0046373 | A1 | 2/2019 | Coulter et al. |
| 2019/0046376 | A1 | 2/2019 | Chiacchira et al. |

FOREIGN PATENT DOCUMENTS

| | | | |
|---|---|---|---|
| EP | 0727298 | A1 | 8/1996 |
| EP | 0727298 | B1 | 8/1999 |
| EP | 2489341 | A2 | 8/2012 |
| EP | 2531159 | A2 | 12/2012 |
| EP | 2619724 | A2 | 7/2013 |
| EP | 2918255 | A1 | 9/2015 |
| JP | H06125942 | A | 5/1994 |
| JP | 2003140631 | A | 5/2003 |
| KR | 20130076922 | A | 7/2013 |
| WO | 0101913 | A1 | 1/2001 |
| WO | 2006089399 | A2 | 8/2006 |
| WO | 2011097569 | A2 | 8/2011 |
| WO | 2012040554 | A2 | 3/2012 |
| WO | 2014021873 | A1 | 2/2014 |
| WO | 2015148578 | A2 | 10/2015 |
| WO | 2015157402 | A1 | 10/2015 |
| WO | 2015171365 | A1 | 11/2015 |
| WO | 2016123595 | A1 | 8/2016 |
| WO | 2016196403 | A1 | 12/2016 |
| WO | 2016200556 | A1 | 12/2016 |
| WO | 2017027427 | A1 | 2/2017 |
| WO | 2017031111 | A1 | 2/2017 |
| WO | 2017061471 | A1 | 4/2017 |
| WO | 2017124056 | A1 | 7/2017 |
| WO | 2017201513 | A1 | 11/2017 |
| WO | 2018026979 | A1 | 2/2018 |
| WO | 2018154819 | A1 | 8/2018 |
| WO | 2018203476 | A1 | 11/2018 |
| WO | 2018216387 | A1 | 11/2018 |

OTHER PUBLICATIONS

Astral Healthcare, "Opthalmology Day Surgery Chair Webpage", Apr. 2018, http://astralhealthcare.com/?product=opthalmology-day-surgery-chair, 6 pages.

Campbell, Mikey, "Apple Expected to Replace Touch ID With Two-Step Facial, Fingerprint Bio-Recognition Tech", Apple Insider, Jan. 21, 2017, http://iphone.appleinsider.com/articles/17/01/21/apple-expected-to-replace-touch-id-with-two-step-facial-fingerprint-bio-recognition-tech, 4 pages.

Doge Medical, "Doc Classic—DOC Surgery Chairs Webpage", 2014, 2 pages, https://web.archive.org/web/20140214203605/http://www.dogemedical.com/pages/en/products/surgery-chairs/doc-classic.php?lang=EN.

English language abstract and machine-assisted English translation for CN 101789230 extracted from espacenet.com database on Aug. 30, 2018, 31 pages.

English language abstract and machine-assisted English translation for JP 2003-140631 extracted from espacenet.com database on Aug. 30, 2018, 19 pages.

English language abstract and machine-assisted English translation for KR 2013-0076922 A extracted from espacenet.com database on Aug. 16, 2018, 8 pages.

English language abstract and machine-assisted English translation for WO 2017/061471 extracted from espacenet.com database on Mar. 25, 2019, 26 pages.

English language abstract and machine-assisted English translation for WO 2018/154819 extracted from espacenet.com database on Mar. 25, 2019, 35 pages.

English language abstract and machine-assisted English translation for WO 2018/203476 extracted from espacenet.com database on Mar. 25, 2019, 37 pages.

English language abstract and machine-assisted English translation for WO 2018/216387 extracted from espacenet.com database on Mar. 25, 2019, 43 pages.

English language abstract for DE 195 05 162 C1 extracted from espacenet.com database on Aug. 16, 2018, 1 page.

English language abstract for EP 0 727 298 A1 extracted from espacenet.com database on Aug. 16, 2018, 1 page.

English language abstract for EP 0 727 298 B1 extracted from espacenet.com database on Aug. 16, 2018, 1 page.

Hall, Stephen, "Nest's 3rd Generation Thermostat Gets Some New Views for Its Farsight Feature", 9 to 5 Google, Jun. 14, 2016, https://9to5google.com/2016/06/14/nest-3rd-gen-thermostat-views-farsight/, 4 pages.

Hill-Rom, "Centrella Smart+Bed Brochure" 2017, 11 pages.

Imore, "How to Use Night Shift on your iPhone or iPad", video also found at https://www.imore.com/night-shift, Nov. 1, 2017, 12 pages.

Recliners.la "Stellar 550 Large Lift Chair Recliner Webpage", Apr. 2018, https://www.recliners.la/products/ultra-comfort-stellar-550-large-lift-chair, 4 pages.

Stryker Medical, "InTouch Critical Care Bed Operations Manual", Aug. 2014, 125 pages.

Stryker, "InTouch Critical Care Bed Model FL27 (2130/2140) Operations Manual—Optional Pendant Control", 2130-009-001 Rev C, Apr. 2008, p. 25.

Supportec-Trade, "Portfolilio Webpage", 2017, https://supportec-trade.nl/en, 2 pages.

U.S. Appl. No. 16/019,973, filed Jun. 27, 2018, 90 pages.

U.S. Appl. No. 16/019,986, filed Jun. 27, 2018, 57 pages.

U.S. Appl. No. 16/020,003, filed Jun. 27, 2018, 37 pages.

U.S. Appl. No. 16/020,052, filed Jun. 27, 2018, 48 pages.

U.S. Appl. No. 16/020,068, filed Jun. 27, 2018, 125 pages.

U.S. Appl. No. 16/020,085, filed Jun. 27, 2018, 67 pages.

U.S. Appl. No. 62/525,359, filed Jun. 27, 2017.

U.S. Appl. No. 62/525,363, filed Jun. 27, 2017.

U.S. Appl. No. 62/525,368, filed Jun. 27, 2017.

U.S. Appl. No. 62/525,373, filed Jun. 27, 2017.

U.S. Appl. No. 62/525,377, filed Jun. 27, 2017.

Youtube, "Memory Seat Escape Video", Nov. 4, 2013, https://www.youtube.com/watch?v=xlghNmAK-7A, 1 page.

Youtube, "Microsoft HoloLens: Partner Spotlight with Stryker Communications Video", Feb. 21, 2017, https://www.youtube.com/watch?v=FTPxUGRGpnA, 3 pages.

* cited by examiner

PATIENT SUPPORT SYSTEMS AND METHODS FOR ASSISTING CAREGIVERS WITH PATIENT CARE

CROSS REFERENCE TO RELATED APPLICATIONS

This application is a Continuation of U.S. patent application Ser. No. 16/020,085 filed on Jun. 27, 2018, which claims priority to and the benefit of U.S. Provisional Patent Application No. 62/525,363 filed on Jun. 27, 2017, the disclosures of each of which are hereby incorporated by reference in their entirety.

BACKGROUND

Patient support systems facilitate care of patients in a health care setting. Patient support systems comprise patient support apparatuses such as, for example, hospital beds, stretchers, cots, tables, wheelchairs, and chairs. A conventional patient support apparatus comprises a base and a patient support surface upon which the patient is supported. Often, the patient support apparatus has one or more powered devices to perform one or more functions on the patient support apparatus. These functions can include lifting and lowering the patient support surface, raising a patient from a slouched position, turning a patient, centering a patient, extending a length or width of the patient support apparatus, and the like. When a user such as a caregiver wishes to operate a powered device to perform a function, the user actuates a user interface. Conventional user interfaces may comprise a panel of buttons configured to selectively operate the various operational functions of the patient support apparatus.

The number and complexity of the operational functions integrated into the patient support apparatus continue to increase, and the evolution of user interfaces has been commensurate. Yet increasingly advanced user interfaces are inherently more difficult to operate, particularly to users not familiar with their operation. Users experiencing difficulty with operating the user interface lack adequate guidance and troubleshooting tools. Therefore, a need exists in the art for a patient support system providing improved guidance and/or troubleshooting tool to control the operations of the patient support apparatus. There is a further need for the guidance and/or troubleshooting tools to be easily and readily accessible through the user interface of the patient support apparatus itself.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
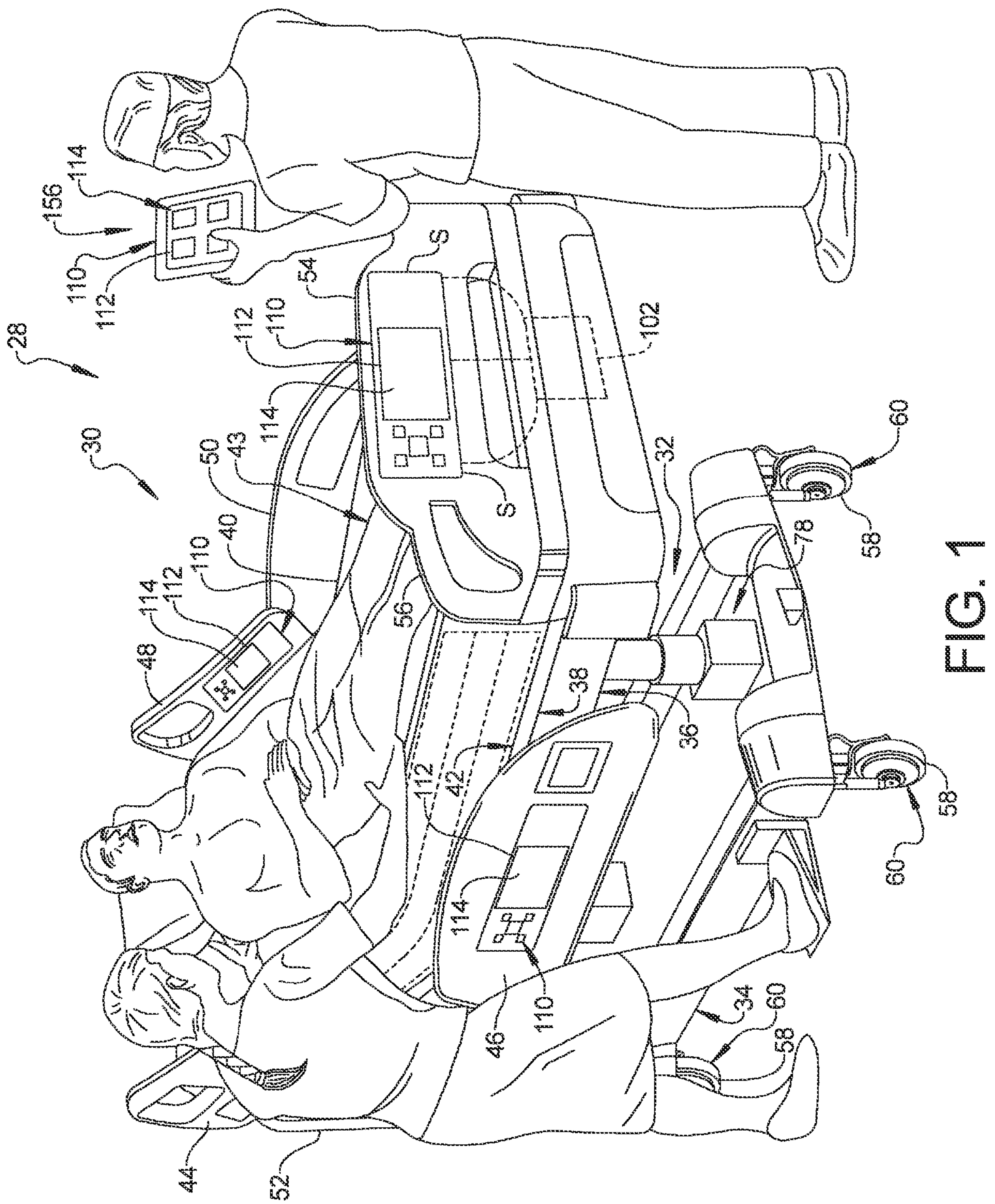
FIG. 1 is perspective view of a patient support apparatus.

FIG. 1 shows a patient support system 28 comprising a patient support apparatus 30 for supporting a patient. The patient support apparatus 30 illustrated in FIG. 1 comprises a hospital bed. In other embodiments, the patient support apparatus 30 may comprise a stretcher, cot, table, wheelchair, chair, or similar apparatus utilized in the care of a patient.

A support structure 32 provides support for the patient. The support structure 32 illustrated in FIG. 1 comprises a base 34 and an intermediate frame 36. The intermediate frame 36 is spaced above the base 34. The support structure 32 also comprises a patient support deck 38 disposed on the intermediate frame 36. The patient support deck 38 comprises several sections, some of which pivot or otherwise articulate relative to the intermediate frame 36, such as a fowler section, a seat section, a thigh section, and a foot section. The patient support deck 38 provides a patient support surface 42 upon which the patient is supported.

A mattress 40 is disposed on the patient support deck 38. The mattress 40 comprises a secondary patient support surface 43 upon which the patient is supported. The base 34, intermediate frame 36, patient support deck 38, an 1 patient support surfaces 42, 43 each have a head end 45 and a foot end 47 corresponding to a designated placement of the patient's head and feet on the patient support apparatus 30. The construction of the support structure 32 may take on any known or conventional design, and is not limited to that specifically set forth above. In addition, the mattress 40 may be omitted in certain embodiments, such that the patient rests directly on the patient support surface 42.

Side rails 44, 46, 48, 50 are coupled to the intermediate frame 36 and thereby supported by the base 34. A first side rail 44 is positioned at a right head end of the intermediate frame 36. A second side rail 46 is positioned at a right foot end of the intermediate frame 36. A third side rail 48 is positioned at a left head end of the intermediate frame 36. A fourth side rail 50 is positioned at a left foot end of the intermediate frame 36. If the patient support apparatus 30 is a stretcher or a cot, there may be fewer side rails. The side rails 44, 46, 48, 50 are movable between a raised position in which they block ingress into and egress out of the patient support apparatus 30, one or more intermediate positions, and a lowered position in which they are not an obstacle to such ingress and egress. In still other configurations, the patient support apparatus 30 may not include any side rails.

A headboard 52 and a footboard 54 are coupled to the intermediate frame 36. In other embodiments, when the headboard 52 and the footboard 54 are included, the headboard 52 and the footboard 54 may be coupled to other locations on the patient support apparatus 30, such as the base 34. In still other embodiments, the patient support apparatus 30 does not include the headboard 52 and/or the footboard 54.

Wheels 58 are coupled to the base 34 to facilitate transport over floor surfaces. The wheels 58 are arranged in each of four quadrants of the base 34 adjacent to corners of the base 34. In the embodiment shown, the wheels 58 are caster wheels able to rotate and swivel relative to the support structure 32 during transport. Each of the wheels 58 forms part of a caster assembly 60. Each caster assembly 60 is mounted to the base 34. It should be understood that various configurations of the caster assemblies 60 are contemplated. In addition, in some embodiments, the wheels 58 are not caster wheels and may be non-steerable, steerable, non-powered, powered, or combinations thereof. Additional wheels are also contemplated. For example, the patient support apparatus 30 may comprise four non-powered, non-steerable wheels, along with one or more powered wheels. In some cases, the patient support apparatus 30 may not include any wheels.

Figure 2:
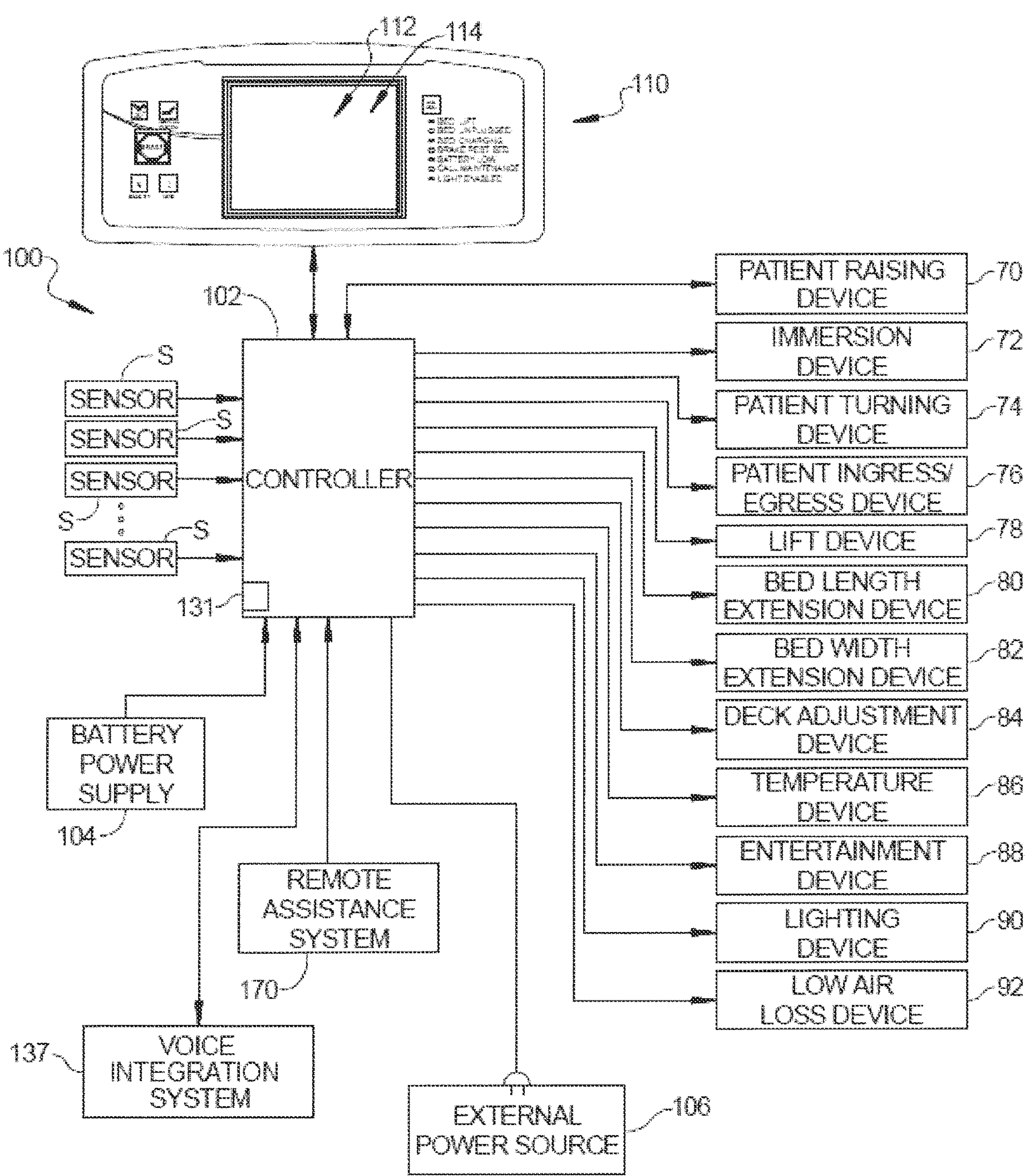
FIG. 2 is a schematic view of a control system.

Referring to FIG. 2, the patient support system 28 may comprise one or more operational devices 70-92 of the patient support apparatus 30, each configured to perform one or more predetermined operational functions. The operational devices 70-92 utilize one or more components that require electricity. The operational devices 70-92 may comprise powered devices for adjustment, such as a patient raising device 70, an immersion device 72, a patient turning device 74, a patient ingress/egress device 76, a lift device 78, a bed length extension device 80, a bed width extension device 82, a deck adjustment device 84, and a low air loss device 92. The operational devices 70-92 may also comprise powered devices for comfort, such as a temperature device 86, an entertainment device 88, and a lighting device 90. Other devices are also contemplated. For instance, operational devices comprising percussion devices, compression devices, vibration devices, and other patient therapy devices may also be employed.

The patient support system 28 comprises a control system 100 to control the operational devices 70-92 of the patient support apparatus 30, and a controller 102. The control system 100 controls the operational devices 70-92, or components thereof, to operate their associated actuators, control their pumps, control their valves, or otherwise cause the operational devices 70-92 to perform one of more of the desired functions. The controller 102 may be a functional subsystem of the control system 100. In other embodiments, the controller 102 may be a discrete system separate from the control system 100. In other words, the control system 100 and the controller 102 may be structurally integrated or separate. In one embodiment, the controller 102 is on-board the patient support apparatus 30 (e.g., coupled to the base 34, the footboard 54, or the like), and in another embodiment, the controller 102 is remotely located from the patient support apparatus 30 and in communication with the operational devices 70-92 disposed on-board the patient support apparatus 30. The controller 102 may communicate with the operational devices 70-92 via wired or wireless connections.

The controller 102 may comprise one or more microprocessors for processing instructions or for processing an algorithm stored in non-transitory memory 131 to control the operational devices 70-92. The control system 100 and/or controller 102 may comprise one or more microcontrollers, subcontrollers, field programmable gate arrays, systems on a chip, discrete circuitry, and/or other suitable hardware, software, or firmware that is capable of carrying out the functions described herein. Power to the operational devices 70-92 and/or the controller 102 may be provided by a battery power supply 104 or an external power source 106. Any type and number of sensors S may be included and in communication with the control system 100 and/or controller 102 to facilitate controlling the operational functions of the patient support apparatus 30.

The operational devices 70-92 may have many possible configurations for performing the predetermined functions of the patient support apparatus 30. Exemplary embodiments of the operational devices 70-92 are described further below, including the patient raising device 70, the immersion device 72, the patient turning device 74, the patient ingress/egress device 76, the lift device 78, the bed length extension device 80, the bed width extension device 82, the deck adjustment device 84, the temperature device 86, the entertainment device 88, and the lighting device 90. Further specifics regarding the exemplary devices are described in commonly owned U.S. patent application Ser. No. 15/353,179, filed on Nov. 16, 2016, which is hereby incorporated by reference herein in its entirety. Numerous devices other than those specifically described are contemplated, including a gatch adjustment device, a cleaning device, a coordinated motion device, a transport device, a cardiopulmonary resuscitation (CPR) device, an information transmission device (to the patient's electronic medical record (EMR) or electronic health record (EHR)), a sit-to-stand assist device, a cough detection device, a sleep detection device, among others. Any of the described and/or contemplated devices may be integrated into the user menus of the present disclosure.

The patient raising device 70 is configured to perform the function of moving the patient from a slouched position towards a non-slouched position by moving the patient towards the head end of the patient support apparatus 30. The patient raising device 70 may comprise a patient raising bladder structure within the mattress 40. The patient raising bladder structure may comprise patient raising inflation bladders that are connected together longitudinally so that each of the patient raising inflation bladders spans across a majority of a width of the mattress 40 below the patient, and the patient raising inflation bladders span a majority of a length of the mattress 40 below the patient. A progressive inflation scheme with the patient raising bladder structure is used to raise the patient from the slouched position to the non-slouched position. In response to a control signal from the controller 102, the patient raising inflation bladders are inflated and deflated to create a wave-like force directed towards the head end of the patient support apparatus 30 to push the patient toward the head end. In one example, only one of the patient raising inflation bladders is fully inflated at a time to create the wave-like force needed to raise the patient. Once fully inflated, each patient raising inflation bladder begins to deflate and the next adjacent patient raising inflation bladder toward the head end begins to inflate.

The immersion device 72 is configured to equalize and distribute pressure over a greater area of the surface of the body over the mattress 40, allowing for immersion of the patient. The immersion device 72 may comprise a bladder structure within the mattress 40 comprising, for example, elongate bladders spanning a majority of the length of the mattress 40 below the patient. In response to a control signal from the controller 102, the elongate bladders are selectively inflated or deflated to control the immersion of the patient within the mattress 40; i.e., the extent in which the patient "sinks into" the mattress. The bladder structure may also be configured move the patient from an off-center position toward a longitudinal centerline of the mattress 40, such as when the patient has shifted too far to one side or the other of the mattress 40. In response to a control signal from the controller 102, the elongate bladders are selectively inflated to guide the patient toward the longitudinal centerline of the mattress 40 when desired. Movement of the patient toward the longitudinal centerline may not be immediate, but may occur gradually as the elongate bladders remain inflated.

The patient turning device 74 is configured to perform the function of turning the patient and/or providing rotational therapy to the patient. The patient turning device 74 may utilize the patient centering/turning bladder structure as the patient centering device 72. In response to a control signal from the controller 102, the elongate bladders are independently inflated to raise one side or the other of the patient. If used for rotation therapy, then the elongate bladders are used for rotation therapy by sequentially inflating/deflating the elongate bladders to raise one side of the patient to a desired angle, lower the patient, and then raise the other side of the patient to the desired angle such that the patient experiences a side-to-side rotation that shifts pressures between the patient and the mattress 40.

The patient ingress/egress device 76 is configured to perform the function of easing ingress and/or egress of the patient to and/or from the patient support apparatus 30. The patient ingress/egress device 76 comprises a main air bladder positioned within the mattress 40. The main air bladder is sized to extend substantially the full width of the mattress 40 and a majority of the length of the mattress 40. In an exemplary embodiment, the main air bladder comprises a single air bladder that can be inflated and deflated, depending on the needs of the patient or the caregiver. The controller 102 transmits a control signal to fully inflate the main air bladder to ease ingress and egress of the patient. For instance, if the main air bladder is less than fully inflated, e.g., to soften the mattress 40 and provide additional comfort to the patient, it can be difficult for the patient to move across the mattress 40 for ingress or egress. Accordingly, by fully inflating, and stiffening the mattress 40, movement across the mattress 40 can be made easier for the patient.

The lift device 78 is configured to lift and lower the patient between the minimum and maximum heights of the patient support apparatus 30, and intermediate positions therebetween. Referring to FIG. 1, a pair of column lifts are illustrated to perform this function. In other embodiments, the lift device 78 comprises a pair of lift arms vertically extending between the base 34 and the intermediate frame 36. The lift device 78 may comprise electromagnetic, electric, pneumatic, or hydraulic actuators, or other types of linear actuators. In response to a control signal from the controller 102, the lift device 78 operates to raise or lower the patient support surface 42, 43 relative to the base 34.

The bed length extension device 80 is configured to perform the function of adjusting a length of the patient support apparatus 30 to accommodate patients of greater than average height. In an exemplary embodiment, the bed length extension device 80 comprises a pair of actuators to move a bed extension between an unextended position and extended positions with respect to the intermediate frame 36. In some embodiments, the bed extension is movable from zero to at least twelve inches from the unextended position to a fully-extended position. In other embodiments, the bed extension is able to move less or more than twelve inches and may be extendable to any position between the unextended and fully-extended position with the actuators. The bed extension may have two, three, four, or nearly an infinite number of extended positions in which to be adjusted by the actuators.

The bed width extension device 82 is configured to perform a function of adjusting a width of the patient support apparatus 30 to accommodate patients of greater than average width. The bed width extension device 82 may operate in the same manner as the bed length extension device 80. The bed width extension device 82 may comprise two sets of actuators to move four bed extensions between unextended and extended positions with respect to the intermediate frame 36. In some cases only one actuator or one set of actuators is employed. In some embodiments, each of the bed extensions is movable from zero to at least twelve inches from the unextended position to a fully-extended position. In other embodiments, each of the bed extensions is able to move less or more than twelve inches and may be extendable to any position between the unextended and the fully extended position with the actuators. Each of the bed extensions may have two, three, four, or nearly an infinite number of extended positions in which to be adjusted by the actuators.

The deck adjustment device 84 is configured to articulate one or more of the deck sections of the patient support apparatus 30. In an exemplary embodiment, the deck adjustment device 84 comprises one or more deck actuators to move one or more of the deck sections of the patient support apparatus 30 including but not limited to the fowler section, the seat section, the thigh section, and the foot section. The actuators may comprise electric linear actuators extending between the intermediate frame 36 and the particular deck section being adjusted. For example, in response to a control signal from the controller 102, actuation of the deck actuator raises and lowers the fowler section at various inclination angles relative to the intermediate frame 36. Suitable linear actuators are supplied by LINAK A/S located at Smedevænget 8, Guderup, DK-6430, Nordborg, Denmark. It is contemplated that any suitable deck adjustment system may be utilized in conjunction with the patient support apparatus 30, so long as the deck adjustment is configured to move one or more of the deck sections.

The temperature device 86 is configured to adjust the temperature of the patient, the temperature of patient support apparatus 30, and/or the temperature of the room in which the patient resides for purposes of patient comfort, therapy, or recovery.

An entertainment device 88 may be activated or adjusted for patient comfort or therapeutic purposes. The entertainment device 88 may be activated or adjusted to provide soothing entertainment or background noise to the patient. In some embodiments the entertainment device 88 comprises at least one piece of entertainment equipment (e.g., television, radio, etc.).

The lighting device 90 may comprise one or more light sources and a dimmer apparatus connected to the light sources to provide lighting that makes the patient more comfortable. In some embodiments one or more of the light sources may be adjusted to be on, off, dimmed or brightened to provide soothing lighting to the patient. In other embodiments, active cancelling of noise may also be employed to make the patient more comfortable.

The low air loss device 92 is configured to reduce or relieve pressure and control moisture caused by the body of the patient in contact with the mattress. The low air loss device 92 may comprise bladders (e.g., the elongate bladders of the immersion device 72) that span a majority of the length of the mattress 40 below the patient. Further, the low air loss device 92 comprises microscopic holes within the patient support surface 43 of the mattress 40 that allow air to escape from the elongate bladders. The amount of pressure within each of the elongate bladders may be selectively controlled. The escaped air provides pressure and moisture reduction.

The operational devices 70-92 of the patient support apparatus 30 are controlled by the control system 100 in response to the user providing an input to a user interface 110. Referring to FIGS. 1 and 2, the patient support system 28 comprises the user interface 110 in communication with the controller 102 and configured to receive inputs from the user. Based on the input from the user to the user interface 110, the controller 102 generates and transmits a control signal to control the operational devices 70-92. The user interface 110 may comprise devices capable of being actuated by or receiving inputs from a user, such as the caregiver or the patient. The user interface 110 may be configured to be actuated in a variety of different ways, including but not limited to, mechanical actuation (e.g., hand, foot, finger, etc.), hands-free actuation (e.g., voice, foot, etc.), and the like. Each user interface 110 may comprise a button, a gesture sensing device for monitoring motion of hands, feet, or other body parts of the caregiver (such as through a camera), a microphone for receiving voice activation commands, and a sensor (e.g., infrared sensor such as a light bar or light beam to sense a user's body part, ultrasonic sensor, etc.). It should be appreciated that any combination of user interfaces 110 may also be utilized for any of the operational devices 70-92.

In certain embodiments, the user interface 110 may be provided as a pendant (not shown) coupled to the patient support apparatus 30. The pendant may be handheld and coupled to the patient support apparatus 30 with a tether, which may also include the electrical and data connection. The pendant may serve as the control suite for some or all of the functions of the patient support system 28 described throughout the present disclosure. In certain embodiments, the pendant integrates the entertainment device 88 and the lighting device 90. In particular, the pendant includes a plurality of tactile and/or touch-sensitive buttons for actuating certain features of the entertainment device 88 and the lighting device 90. Exemplary features include "channel up," "channel down," "music up," "music down," "television," "radio," "room lights," "reading lights," and the like. An exemplary pendant suitable for the present application is included on the In-Touch Critical Care Bed manufactured by Stryker Corp. (Kalamazoo, Mich.).

The user interface 110 may be located on one of the side rails 44, 46, 48, 50, the headboard 52, the footboard 54, or other suitable locations. FIG. 1 shows the user interface 110 is located on two of the side rails 46, 48 and the footboard 54. FIG. 1 further shows the user interface 110 located on the footboard 54 and rotatably mounted to the same. Additionally or alternatively, the user interface 110 may also be located on a mobile device 156 (e.g., iWatch®, iPhone®, iPad®, or similar electronic devices). FIG. 1 shows a caregiver holding the mobile device 156 comprising a touchscreen display 114 with the user interface 110. The user interface 110 is configured to receive the inputs from the user in any suitable manner including, but not limited to, mechanical actuation, voice commands, and gesturing. The user typically provides the input to the user interface 110 through the touch of a tactile or virtual button. In response to the inputs from the user, the user interface 110 may generate input signals. In one preferred embodiment, the controller 102 receives the input signals from the user interface 110 based on the inputs from the user to the user interface 110.

In some embodiments, the user interface 110 comprises a voice integration system 137 in communication with the controller 102. The voice integration system 137 comprises a voice actuation interface such as microphone in communication with the controller 102 to receive voice commands from the user. The microphone may be mounted to the base 34, the intermediate frame 36, the side rails 44, 46, 48, 50, the headboard 52, the footboard 54, or other suitable locations on the patient support apparatus 30. The microphone may also be located on the mobile device 156 or otherwise remote from the patient support apparatus 30. Based on the vocal input from the user provided to the voice integration system 137, the voice integration system 137 provides input signals to the controller 102 for functions to be disclosed.

The patient support system 28 further comprises an information output device 112 in communication with the controller 102 and configured to provide instructions to the user, such as the caregiver or the patient. In one embodiment, the information output device 112 comprises a display displaying the instructions and other information to the user. In another embodiment, the information output device 112 comprises speakers providing audible instructions to the user. Combinations of the display and speakers are preferred in many embodiments. In a further preferred embodiment, the user interface 110 and the information output device 112 are embodied on the touchscreen display 114. Capacitive touchscreens and other types of displays capable of receiving a touch-sensitive input may be employed.

The user interface 110 and/or the information output device 112 may be located on one or more of the side rails 44, 46, 48, 50, the headboard 52, the footboard 54, or other suitable locations. In the embodiment shown in FIG. 1, the user interface 110 and the information output device 112 are located on two of the side rails 46, 48 and the footboard 54. Additionally or alternatively, the user interface 110 and the information output device 112 may also be located on the mobile device 156 or the pendant previously described.

Figure 3:
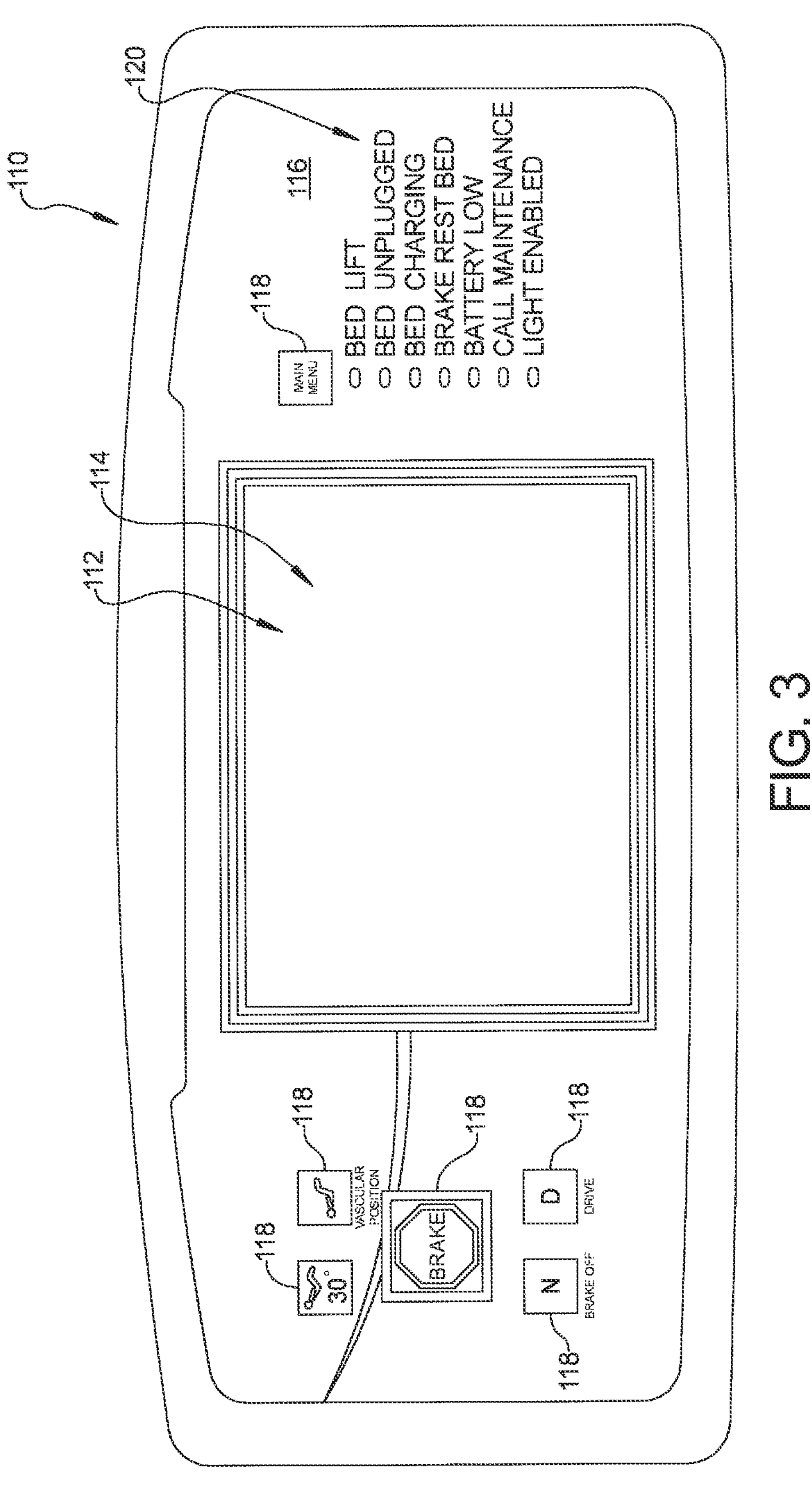
FIG. 3 a perspective view of a user interface and an information output device.

Referring to FIG. 3, an exemplary user interface is shown. The user interface 110 may comprise a front cover 116. One or more virtual or tactile buttons 118 may be disposed on the front cover 116 in any suitable configuration. The buttons 118 integrated into the front cover 116 may be indicative of operational functions of the patient support apparatus 30, particularly those more frequently used by caregivers. FIG. 3 shows tactile buttons associated with an emergency brake feature, a "drive" feature, and a "brake off" feature, among others. Status indicators 120 may be disposed on the front cover 116 in any suitable configuration. FIG. 3 illustrates several status indicators in columnar form with each status indicator 120 comprising a light (e.g., light emitting diode) corresponding to a particular status (e.g., bed unplugged, bed charging, etc.). The status indicators 120 provide users with warnings and other relevant information without needing to navigate the user menus 130 of a software application. Lastly, FIG. 3 shows the information output device 112 within the front cover 116 and positioned intermediate the buttons 118 and the status indicators 120. The information output device 112 of FIG. 3 is the touchscreen display 114 and comprises a portion of the user interface 110. The touchscreen display 114, as described throughout the present disclosure, is configured to provide instructions, information and other output (e.g., graphics) to the user, and further configured to receive input from the user, such as through manual actuation, as described above.

Figure 4:
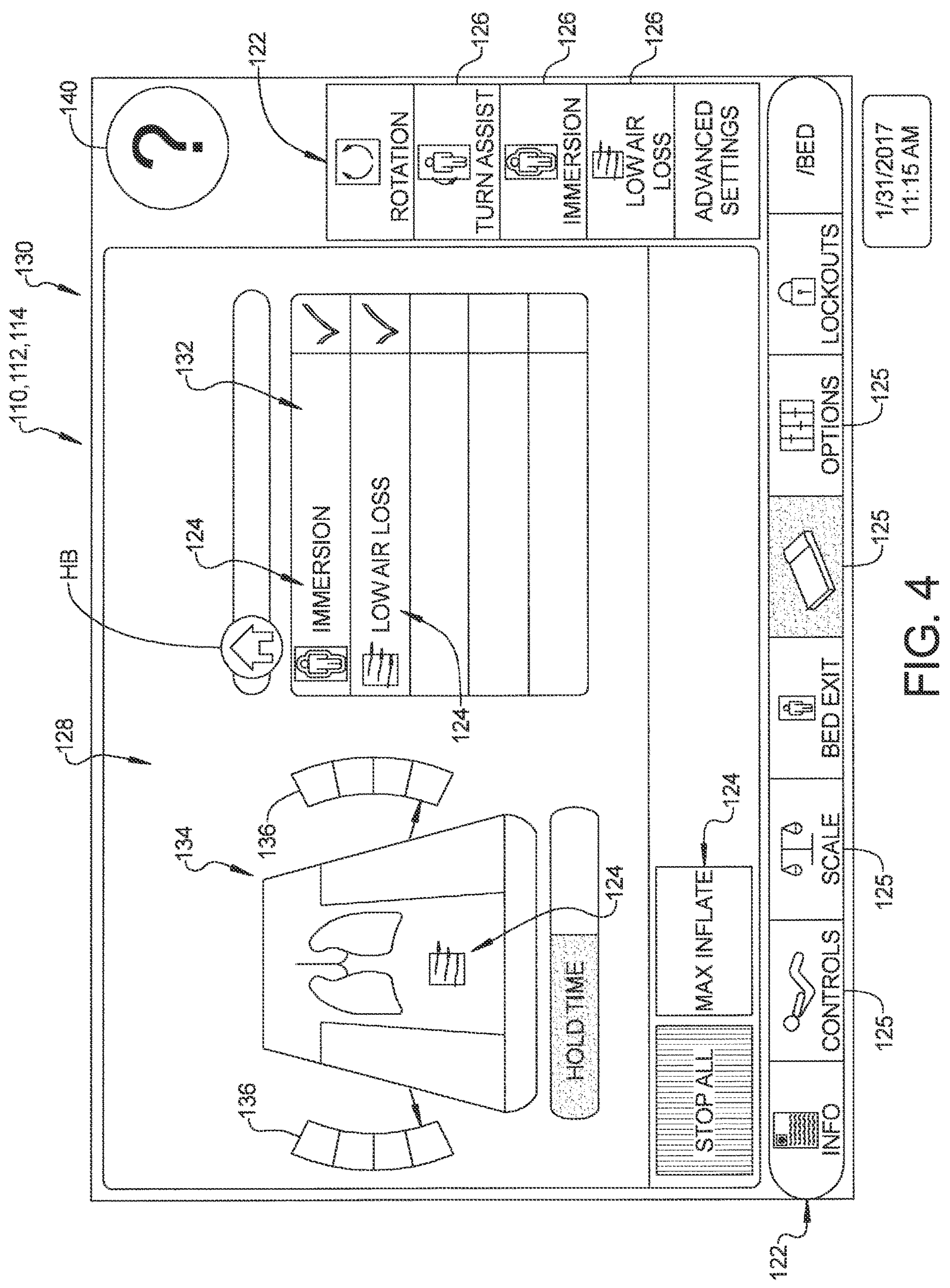
FIG. 4 is a touchscreen display comprising the information output device of FIG. 3 and a portion of the user interface of FIG. 3, with the touchscreen display displaying a user menu.

The controller 102 may be configured to execute the software application. The software application is configured to display user menus 130 navigable by the user to control the operational functions of the patient support apparatus 30, such as to control the operational devices 70-92. In general, the user menus 130 may comprise any suitable output displayed with the information output device 112 to facilitate efficient operation of the patient support system 28. Any suitable format of the user menus 130 is contemplated, including but not limited to lists, grids and/or arrays of text, graphics and/or icons comprising indicia 124. The indicia 124, as used herein, may comprise text, graphics, and the like, selectable by the user with the user interface 110. In the exemplary embodiments illustrated in FIGS. 4-12, the indicia 124 is within a working area 128 of the user menu 130. Indicia 125 representative of predetermined one or more of submenus 152 (see, e.g., FIG. 8) and/or indicia 126 representative of one of more operational functions of the patient support apparatus 30 may be provided and arranged on one or more taskbars 122. FIG. 4 shows a horizontal one of the taskbars 122 comprising the indicia 125 and a vertical one of the taskbars 122 comprising the indicia 126. The taskbars 122 remain generally static (e.g., other than highlighting of selected indicia), whereas the working area 128 is provided to display generally dynamic text, graphics, and other media associated with any particular one of the user menus 130. Through actuation of the user interface 110 (e.g., touching virtual buttons of the touchscreen display 114), the user may navigate through the user menus 130 of the software application of the patient support system 28.

The user menus 130 may comprise a home menu (not shown). The home menu may comprise the output provided by the information output device 112 upon initializing the software application such as after non-use of the user interface 110 for a predetermined period, a reset of the system, or the like. The home menu may comprise one of the user menus 130 provided by the information output device 110 in response to the user actuating the home button HB. The user menus 130 may further comprise the submenus 152. The submenus 152, in a general sense, are the output provided by the information output device 112 in response to a user selection of the indicia 124, 125, 126 displayed visually on the information output device 110. Often, the submenus 152 provide indicia 124, 125, 126 representative of operational functions of the patient support apparatus 30 more specific relative to the home menu. The submenus 152 may comprise one, two, or three or more submenus for each of the indicia 124, 125, 126 displayed on the home menu. For example, the submenus 152 may comprise primary, secondary and tertiary submenus as the user navigates the software application. FIG. 4 shows an exemplary one of the user menus 130.

Controlling the operational functions of the patient support apparatus 30 may require performing several steps with the software application. A navigation protocol may be defined as a series of user-performed actions to control any particular one of the operational functions of the patient support apparatus 30. In one example, the navigation protocol may require the user to provide multiple inputs to the user interface 110 to navigate the user menus 130 to control the desired one or more of the operational functions of the patient support apparatus 30. Should the user accidentally or erroneously provide an incorrect input to the user interface 110, as is not uncommon particularly with touchscreen displays, the information output device 112, in response, may display a submenu 152 unrelated to the desired one or more of the operational functions sought to be operated by the user. The user may have deviated from the navigation protocol. Depending on the familiarity of the user with the software application, touchscreen displays, technology generally, and other factors, any number of undesirable consequences may result. The user may be required to return to the home menu or other previous user menu 130 to reattempt navigating the user menus 130, adding undue time and frustration to the user experience. Alternatively, the user may simply lack the technological savvy to navigate the user menus 130 of the software application. It is therefore one of many advantages of the subject invention to provide improved guidance and/or troubleshooting that is accessible through the user interface 110 and/or information output device 112.

With continued reference to FIG. 4, the user menu 130 comprises the working area 128 providing a selected operations list 132 and an operations graphic 134 representative of the patient support apparatus 30. The selected operations list 132 may comprise the recently selected operational functions of the patient support apparatus 30. In certain embodiments, the text of the selected operations list 132 comprises text representative of the most recently actuated one or more operational devices 70-92, such as the immersion device 72 and the low air loss device 92. In the example of FIG. 4, the most recently used feature of the patient support apparatus 30 was the immersion device 72, and the second most recently used feature was the low air loss device 92. The text may also be indicia 124 selectable by the user to selectively toggle the operation of the corresponding one of the operational devices 70-92, such as from an active or operational state to an inactive state. The selected operations list 132 may provide a checkmark or similar marking to indicate whether the operational devices 70-92 of the patient support apparatus 30 are in the active or inactive states. The area occupied by checkmark may also be actuated by the user to selectively toggle the operation of the corresponding one of the operational devices 70-92 between the active and inactive states. In the exemplary embodiment of FIG. 4, the checkmarks next to the indicia 124 representative of the immersion device 72 and the low air loss device 92 indicate each of those devices are in the active state or operating presently.

The operations graphic 134 of the patient support apparatus 30 may also provide the user with information as to which of the operational devices 70-92 are in active state. For example, FIG. 4 shows arcuate gradients 136 that may indicate that the immersion device 72 is in the active state, with arrows that may be reflective of a particular level or setting of the immersion device 72. FIG. 4 also shows a representation of a box with three curvilinear arrows that may be indicative that the low air loss device 92 is in the active state. The icons (e.g., the box-arrows representation) may match those in the selected operations list 132 and the taskbar 122 such that the user readily identifies which operational function is in the active state. In some embodiments, the operations graphic 134 is configured to be actuated by the user with the user interface 110 to selectively toggle the operation of the corresponding one of the operational devices 70-92. For example, the user may actuate the box-arrows indicia such that the low air loss device 92 moves from the active state to the inactive state. In response to the actuation, the indicia 124 may be removed, and the checkmark next to the indicia 124 representative of the immersion device 72 on the selected operations list 132 may be removed.

Often, the one or more of the operational devices 70-92 to be controlled by the user may not be represented on the home menu (or one of the user menus 130) being displayed with information output device 112. The user may be required to perform one or more user-performed actions (e.g., providing input(s) to the user interface 110) in order to navigate the user menus 130 of the software application such that the user is provided with the option to control the one or more of the operational devices 70-92. Those unfamiliar with navigating the software application may experience appreciable difficulty with doing so.

According to an exemplary embodiment of the present disclosure, the controller 102 is configured to receive input signals from the user interface 110 based on the inputs from the user to the user interface 110. In certain embodiments, the inputs from the user to the user interface 110 comprise the user touching the touchscreen display 114. For any number of reasons, the user may provide a troubleshooting request to the user interface 110. For example, the user may have unsuccessfully attempted to navigate the user menus 130 of the software application to the menu configured to control the desired one or more of the operational devices 70-92. In another example, the user may anticipate difficulty with navigating the user menus 130 and/or prefers to save time by seeking assistance. In certain embodiments, the troubleshooting request comprises a virtual help button 140 on the user interface 110, and more particularly the touchscreen display 114. FIG. 4 shows the virtual help button 140 positioned in an upper-right corner of the touchscreen display 114.

The controller 102 is configured to determine a guidance protocol for the user based on the input signals from the user interface 110. Whereas the navigation protocol may be the user-performed actions performed by the user without the instructions being provided to the user, the guidance protocol comprises the user-performed actions to be performed by the user in response to the instructions provided to the user with the information output device 112. In other words, the navigation protocol may be considered the guidance protocol if the user did not require troubleshooting (i.e., correctly navigated the user menus 130). For example, the guidance protocol is the user-performed actions to be performed after the user has accidentally deviated from the navigation protocol.

Figure 5:
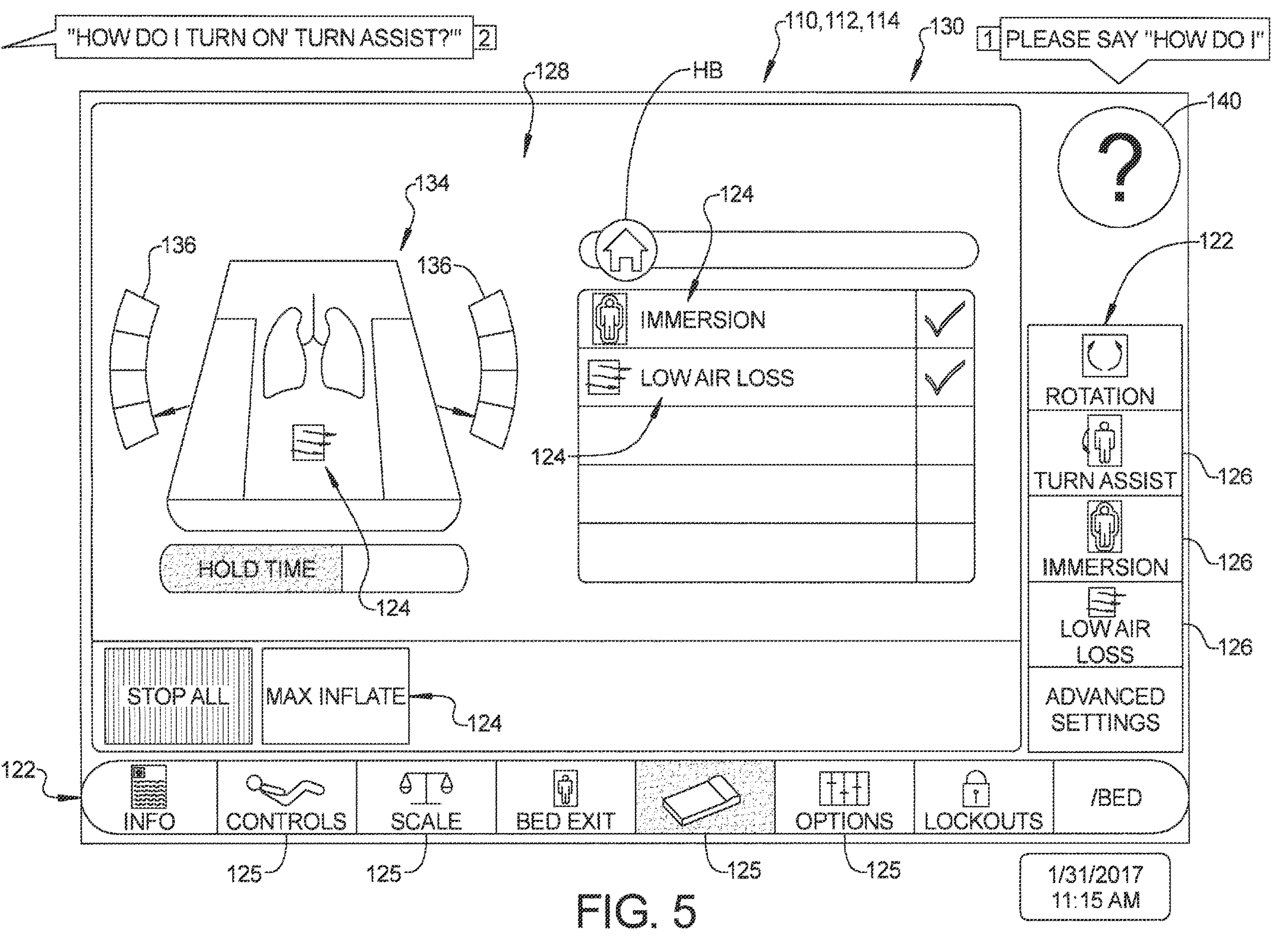
FIG. 5 is the touchscreen display of FIG. 4 displaying a user menu with a troubleshooting request being provided to the user interface.

In certain embodiments, the guidance protocol may comprise a plurality of steps needed to be taken by the user to result in the desired outcome associated with a troubleshooting request from the user provided to the user interface 110. For example, subsequent to the user actuating the virtual help button 140, the information output device 112 outputs a prompt requesting further information. Referring to FIG. 5, the information output device 112 comprising speakers may output a phrase, for example, "Please say 'How do I' and state your question," or "Please say how I can be of assistance." Additionally or alternatively, the information output device 112 comprising the touchscreen display 114 may display the output visually to invite the user to vocally provide specifics of the troubleshooting request to the voice integration system 137. The present disclosure also contemplates the information output device 112 comprising the touchscreen display 114 may provide the user with a list of frequently asked questions (FAQs). In such an embodiment, the user may select, via the touchscreen display 114, one of the FAQs that the user perceives to be most related to subject matter of the troubleshooting request. Providing the list of FAQs may provide additional or alternative means for the user to provide the troubleshooting request to the user interface 110. Other manners by which the troubleshooting request may be provided are described throughout the present disclosure.

The user provides the troubleshooting request, and the troubleshooting request comprises the input from the user to the user interface 110. The input signals received by the controller 102 from the user interface 110 are based on the input comprising the troubleshooting request. The controller determines the guidance protocol determined by the input signals. The guidance protocol may comprise a plurality of steps needed to be taken by the user to result in the desired outcome associated with the troubleshooting request. For example, should the troubleshooting request involve operating the immersion device 72, the guidance protocol comprises the steps needed to be taken in order to do so. The steps may each comprise one or more instructions provided to the user with the information output device 112. The instructions 160 may comprise first and second instructions, first and second steps, and the like. The controller 102 is further configured to provide a first of the instructions to the user with the information output device 112, and provide a second one of the instructions to the user with the information output device 112 in response to the user performing a first of the user-performed actions.

Figure 6:
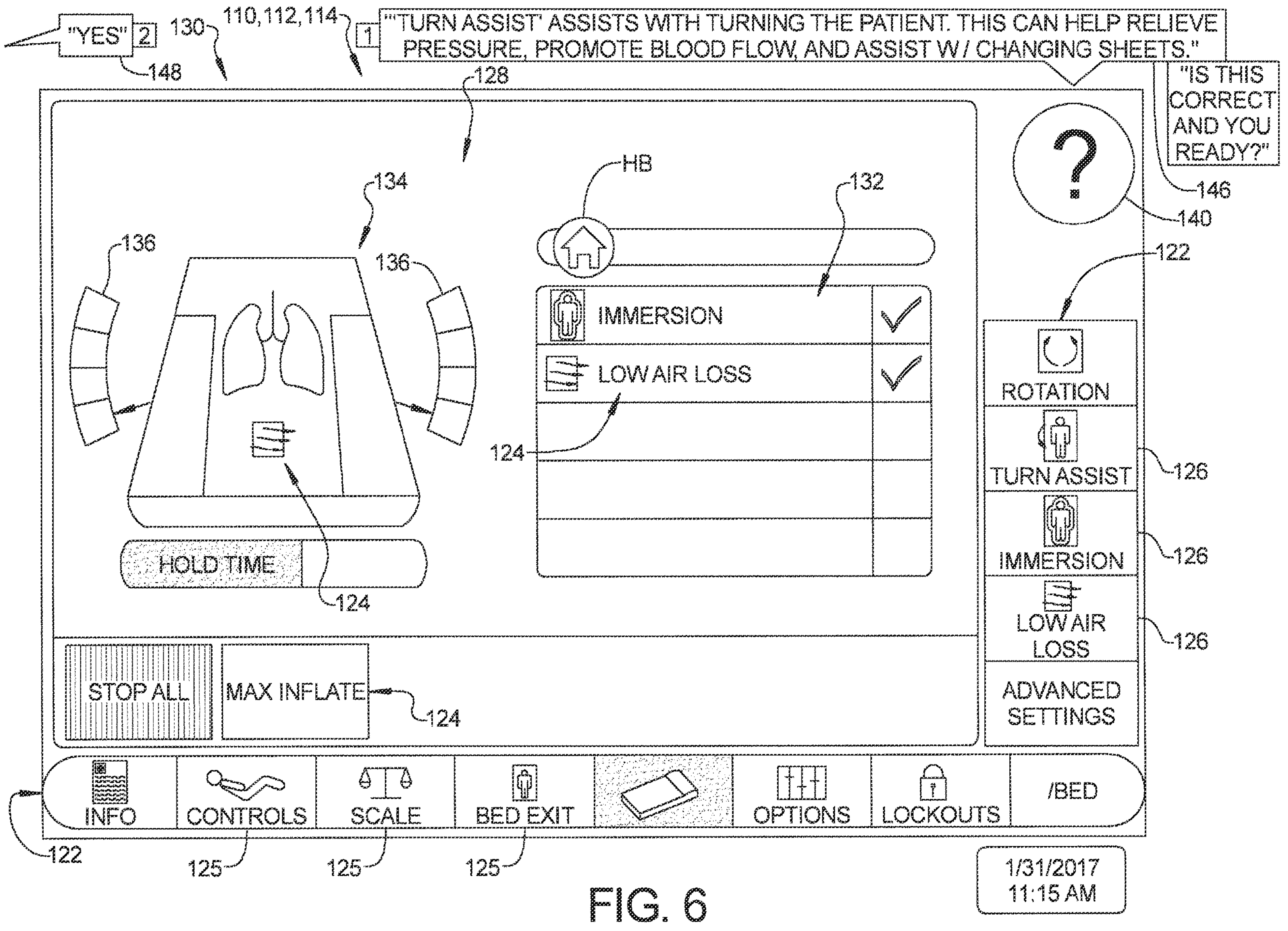
FIG. 6 is the touchscreen display of FIG. 4 displaying the user menu with the information output device further providing a confirmatory request.

An exemplary operation of the guidance and troubleshooting is described with reference to FIGS. 4-9. In the present embodiment, the user interface 110 and the information output device 112 are embodied with the touchscreen display 114. The user interface 110 may further comprise the voice integration system 137, and the information output device 112 may further comprise the speakers. In such a configuration, the user may perform the user-perform actions through speaking and/or touching the touchscreen display 114, and receive instructions audibly and/or visually. One of the user menus 130 is displayed on the touchscreen display 114, and the user actuates the virtual help button 140 displayed on the touchscreen display 114. In response, the information output device 112 provides output to the user requesting further information as described above and shown in FIG. 5. The user provides the further information comprising the troubleshooting request with the user interface 110. In FIG. 6, the user provides the requested information and verbally inputs to the voice integration system 137, for example, "How do I turn on 'Turn Assist?'" The voice integration system 137 receives the input and transmits the input signals to the controller. The controller 102 determines the guidance protocol based on the input signals, such as by matching the received voice input to a database associating keywords with the appropriate one or more operational devices 70-92. In this example, based on the use of the words "turn" and "assist," the controller 102 determines the guidance protocol comprises the user-performed actions to be performed by the user in order to operate the patient turning device 74. Other, perhaps less precise, voice inputs to the voice integration system 137 may require more elaborate determinations by the controller 102 as to the intentions of the user. For example, the user may say to the voice integration system 137, "He has bed sores," or "I need help changing the sheets." Utilizing artificial intelligence (AI), algorithms, a database of keyword associations, and the like, the controller 102 is configured to determine the most relevant guidance protocol to present to the user. In certain embodiments, the information output device 112 may be configured to provide options for the user to further consider and from which to select. For example, in response to the user inquiring about bed sores, the touchscreen display 114 may provide a pop-up window providing indicia 124 representative of the patient turning device 74, as well as the immersion device 72 and the low air loss device 92, each of which may be desirable to alleviate the pressure that causes bed sores. Options may be provided in every instance or in some instances when the controller 102 is unable to determine the guidance protocol for a particular operation with a confidence index above a confidence threshold. The confidence index may be provided to the user such that the user receives feedback as to how the system perceived the troubleshooting request. Subsequently, the user selects one of the options with the selection comprising the troubleshooting request that is provided as an input signal to the controller 102.

In some embodiments, the information output device 112 may provide the user with a confirmatory request 146. The confirmatory request 146 may simply repeat the provisionally selected one of the operational functions of the operational devices 70-92 (e.g., "Turn Assist" of the patient turning device 84), and/or provide additional information about the same. FIG. 6 shows the information output device 112 providing audible output including "'Turn Assist' assists with turning the patient. This can help to relieve pressure, promote blood flow, and assist with changing sheets. Is this correct and are you ready?" The user provides a confirmatory response 148 to the user interface 110, such as by verbally responding "Yes" or actuating the user interface 110 in a suitable manner.

Figure 7:
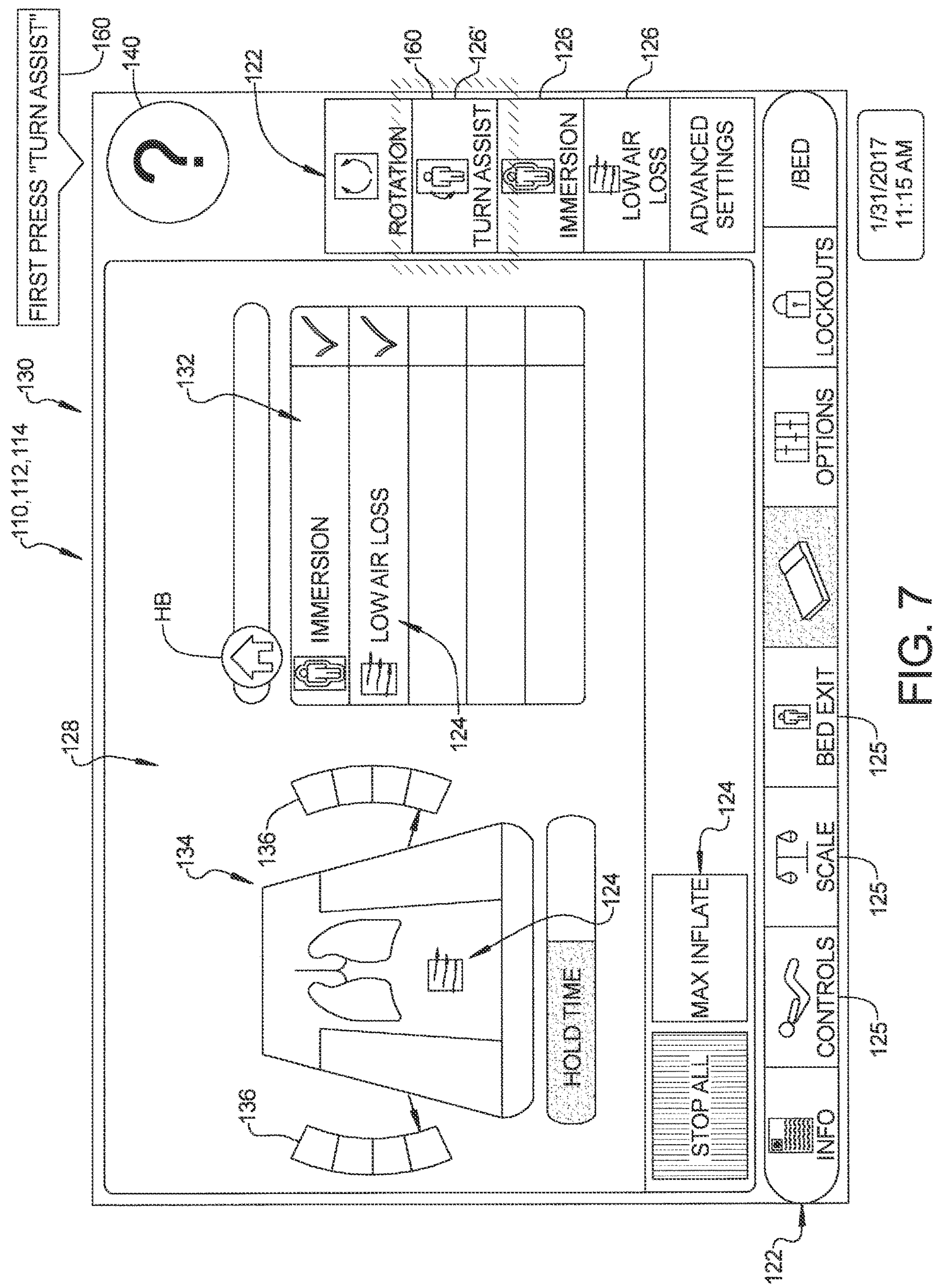
FIG. 7 is the touchscreen display of FIG. 4 displaying the user menu of FIG. 4 with the information output device providing a first instruction or step to the user. Indicia of the user menu corresponding to the first instruction or step is visually emphasized. The user provides a first user-performed action or input to the user interface in response to the first instruction or step. The first user-performed action or input may comprise an initial selection.

The controller 102 is configured to provide a first instruction to the user with the information output device 112. The first instruction may be the first of a plurality of instructions 160 or a first step of a plurality of steps. As previously mentioned the touchscreen display 114 may comprise the taskbar 122 with indicia 125, 126 representative of operational functions of the patient support apparatus 30. The indicia 125, 126 may be selectable by the user with the user interface 110, in many cases the touchscreen display 114. In certain embodiments, providing the instructions 160 to the user on the touchscreen display 114 comprises the controller 102 being configured to visually emphasize on the touchscreen display 114 at least one of the indicia 124, 125, 126. FIG. 7 shows the first instruction is provided to the user, with the first instruction comprising visually emphasizing the indicia 126' associated with "Turn Assist" and representative of the patient turning device 84 of the patient support apparatus 30. Additionally or alternatively, the information output device 112 audibly provides the first instruction to the user to "First press 'Turn Assist.'"

The visual emphasis may include providing elements to and/or modifying elements of the indicia 124, 125, 126, such as line, shapes, forms, values, colors, textures, space, and the like, to focus the user on the emphasized indicia 124, 125, 126. In certain embodiments, color(s) of the indicia 124, 125, 126 (e.g., background or foreground color) may be changed to provide contrast different from the other displayed indicia 124, 125, 126. It should be appreciated that the term color comprises hue, tint, shade, tone, lightness, saturation, intensity, and/or brightness such that references made herein to different colors also encompasses different hue, tint, tone, lightness, saturation, intensity, and/or brightness. In certain embodiments, shapes may be provided and arranged in a manner to focus the user. FIG. 7 shows the visual emphasis comprising a ring or halo around the indicia 126'. In another example, a marking (e.g., an arrow, as asterisk, etc.) or image (e.g., clipart) may be provided to focus the user on the emphasized indicia 124, 125, 126. In still another example, the indicia 124, 125, 126 may be highlighted, such as underlining and/or coloring text or its background. Other types of visual emphasis are contemplated, for example, altering the size, shape, look and/or feel of the indicia 124, 125, 126.

The guidance protocol further comprises the user-performed actions to be performed by the user in response to the instructions provided to the user. In other words, in response to the first of the instructions 160 (e.g., the visual emphasis of indicia 126' and/or audible instruction(s)), the user performs a first user-performed action corresponding to the first instruction. In preferred embodiments, the first user-performed action is performing the action suggested by the information output device 112. In the example shown in FIG. 7, the first user-performed action in response to the first instruction is actuating the indicia 126' associated with the "Turn Assist."

The user may perform a user-performed action that deviates from the first instruction provided to the user. For example, the user may accidentally actuate one of the indicia 124, 125, 126 other than the indicia 126' visually emphasized and/or audibly described with the first instruction. In certain embodiments, the controller 102 is configured to determine whether the performed user-performed action is the first user-performed action. In other words, the controller 102 determines whether the input provided to the user interface 110 subsequent to providing the first of the instructions 160 correlates, matches, or is otherwise correct based on the first instruction provided to the user. Should the user-performed action be incorrect, the resulting information being displayed on the touchscreen display 114 may deviate from the guidance protocol. In exemplary embodiments, the controller 102 may be configured to automatically determine an updated guidance protocol. The updated guidance protocol is directed to effectuating the same end result as the guidance protocol, but it may require greater, fewer, or different instructions in order to achieve the result. For example, the updated guidance protocol may comprise the original guidance protocol, with the addition of the user first selecting a virtual "Back" button BB (see FIGS. 8 and 9). In the example, the updated guidance protocol provides instructions (e.g., the visual emphasis and/or audible instruction) for the user to actuate the "Back" button BB, after which the user may be returned to the previous one of the user menus 130, after which the guidance protocol may proceed as originally determined. Based on the specific nature of the deviation or error from the guidance protocol, the updated guidance protocol may be more complex (e.g., require additional steps) than actuating the "Back" button BB.

Figure 8:
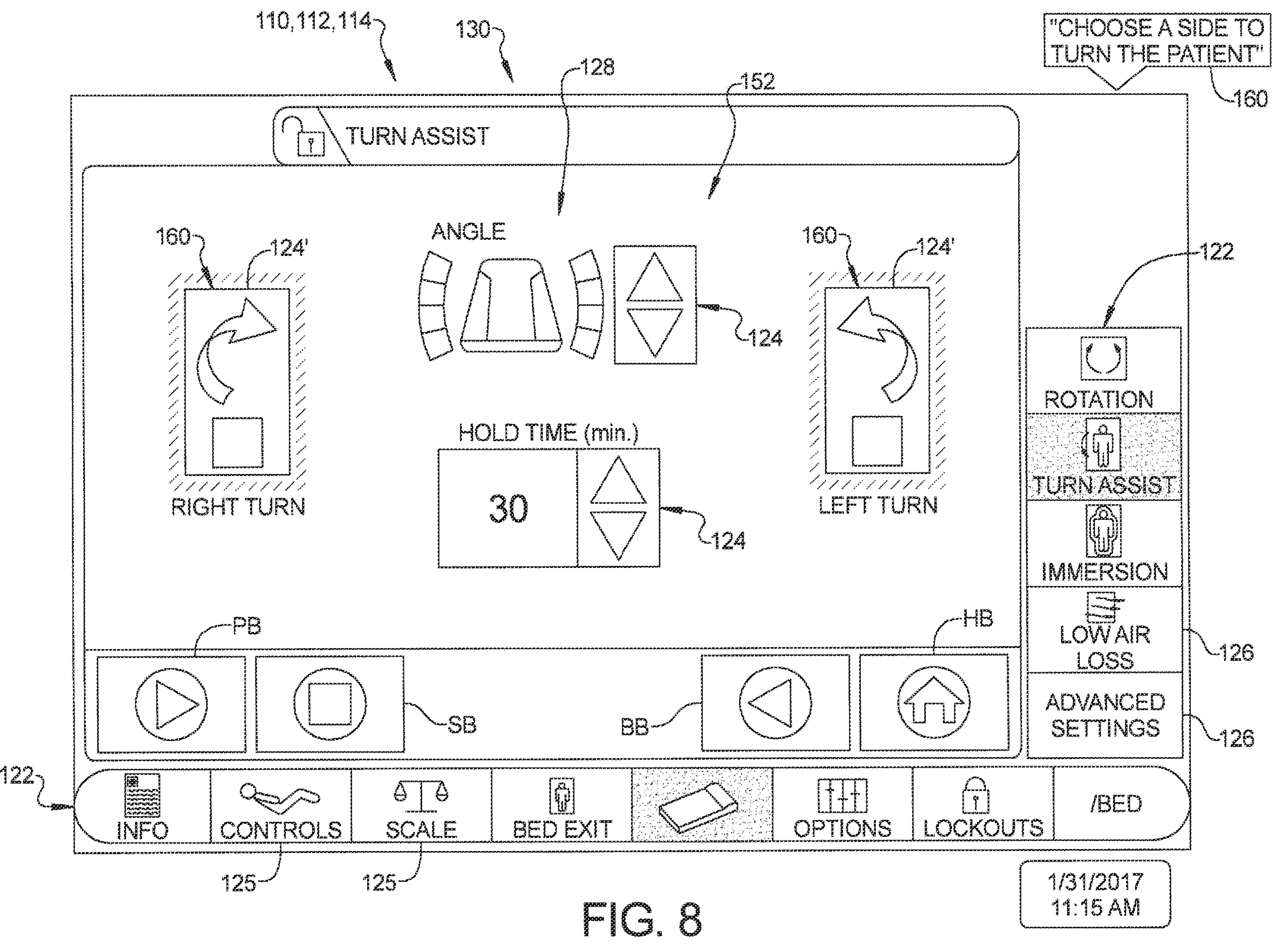
FIG. 8 is the touchscreen display of FIG. 4 displaying a submenu with the information output device providing a second instruction or step to the user. Indicia of the user menu corresponding to the second instruction or step is visually emphasized. The user provides a second user-performed action or input to the user interface in response to the second instruction or step. The second user-performed action or input may comprise an intermediate selection.
Figure 9:
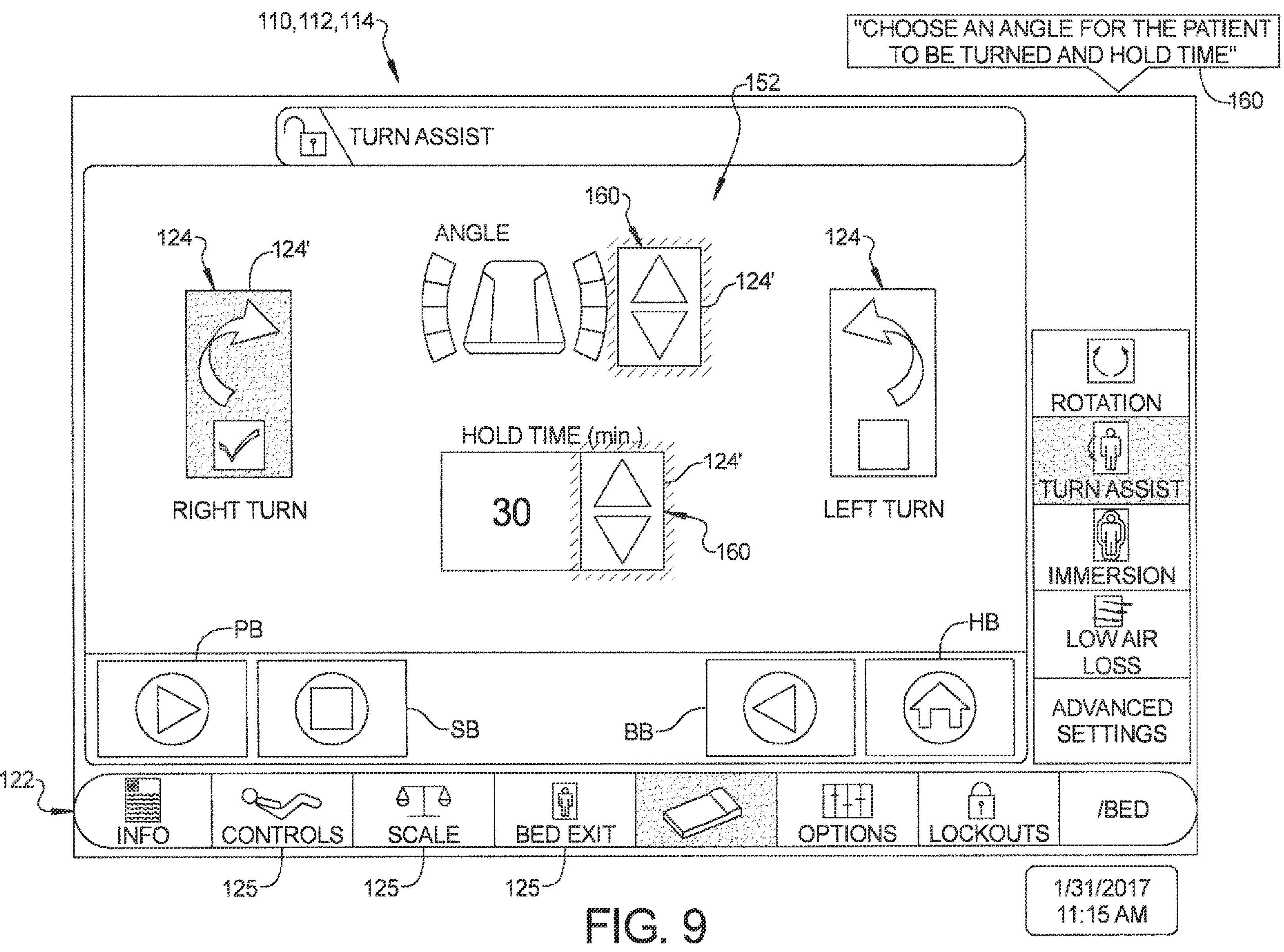
FIG. 9 is the touchscreen display of FIG. 4 displaying the submenu of FIG. 8 with the information output device providing a third instruction or step to the user. Indicia of the user menu corresponding to the third instruction or step is visually emphasized. The user provides a third user-performed action or input to the user interface in response to the third instruction or step. The third user-performed action or input may comprise another intermediate selection.

The user-performed action preferably correlates, matches, or is otherwise correct based on the first instruction provided to the user such that the guidance protocol may proceed as originally determined. The controller 102 is configured to provide a second of the instructions to the user with the information output device 112 in response to the user performing the first of the user-performed actions. Based on the user-performed action of selecting the indicia 126' representative of "Turn Assist," one of the submenus 152 is provided with the information output device 112. Referring to FIG. 8, the submenu 152 comprises the working area 128 having text, graphics, and other information not provided with the other user menu 130 of FIG. 7. In other words, the working area 128 has been dynamically updated with content directed to the "Turn Assist" operation. The submenu 152 of FIG. 8 includes indicia 124 representative of a right turn and a left turn, corresponding to which direction the Turn Assist facilitates turning the patient. The submenu of FIG. 8 further comprises indicia 124 representative of the angle or level to which the patient is turned, and the hold time in which to hold the patient at the angle or level. A title bar may be positioned atop the information output device 112 and describe the subject matter of the submenu 152.

In many respects, providing the second of the instructions 160 is performed in the same manner as providing the first of the instructions 160. Providing the second of the instructions 160 to the user on the touchscreen display 114 comprises the controller 102 being configured to visually emphasize on the touchscreen display 114 at least one of the indicia 124, 125, 126. FIG. 8 shows the visual emphasis comprising a ring or halo around the indicia 124' associated with the right and left turn options. Additionally or alternatively, the information output device 112 audibly provides the second instruction to the user to "Choose a side for the patient to turn." Since two of the indicia 124' have been visually emphasized, particularly together with the audible instructions, it should be understood by the user that a choice is to be made. In response to the instructions 160 provided to the user, the user may perform a second of the user-performed actions. In the present example, the user actuates one of the indicia 124', after which the indicia 124' may be further emphasized to signal to the user that the input was received. For example, the indicia 124' may be highlighted (e.g., changed to a different color or brightness) relative to the other indicia 124' (see FIG. 9).

The guidance protocol may proceed through subsequent iterations of providing instructions 160 or steps in response to user-performed actions consistent with the disclosure above. The guidance protocol may proceed to a subsequent one of the instructions 160 or steps after the user successfully performs the user-performed action, or after indicia such as play button PB is actuated to indicate the user is ready for the next one of the instructions 160 or steps. In some embodiments, the controller 102 is further configured to provide a third of the instructions 160 to the user with the information output device 112 in response to the user performing a second of the user-performed actions. After the user-performed action of selecting the indicia 124 representative of "Right Turn" in FIG. 9, the guidance protocol may provide the third of the instructions 160 comprising the controller 102 being configured to visually emphasize on the touchscreen display 114 at least one of the indicia 124, 125, 126. FIG. 8 shows the visual emphasis comprising a ring or halo around the indicia 124' associated with the "Angle" and the "Hold Time." Additionally or alternatively, the information output device 112 audibly provides the third instruction to the user to "Choose an angle for the patient to be turned and a hold time." Since two of the indicia 124' have been visually emphasized, particularly together with the audible instructions, it should be understood by the user that two of the user-performed actions are required in response to the third of the instructions 160. It should be understood that the guidance protocol may comprise more than one user-performed actions in response to one of the instructions, and in some cases, no user-performed action is required in response to one of the instructions (e.g., one of the instructions are merely explanative).

Figure 10:
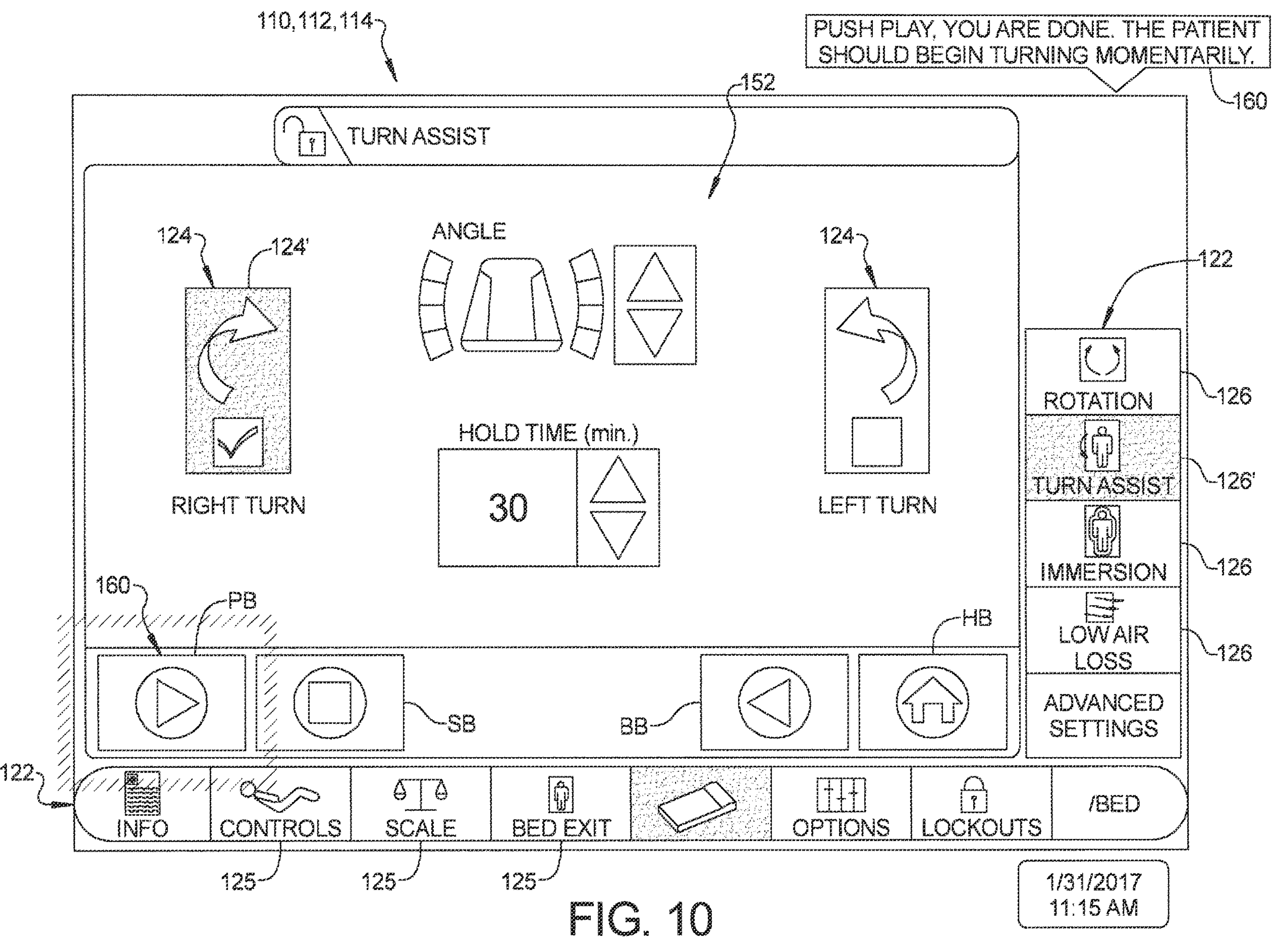
FIG. 10 is the touchscreen display of FIG. 4 displaying the submenu of FIG. 8 with the information output device providing a fourth instruction or step to the user. Indicia of the user menu corresponding to the fourth instruction or step is visually emphasized. The user provides a four user-performed action or input to the user interface in response to the fourth instruction or step. The fourth user-performed action or input may comprise a final selection.

Referring now to FIG. 10, the controller 102 provides a subsequent one of the instructions 160 or steps in response to the user performing the user-performed actions of selecting an angle and a hold time. In FIG. 10, a final one of the instructions comprises providing visual emphasis to the play button PB along with the audible instructions: "Push play, and you are done. The patient should begin turning momentarily." The user performs the user-performed actions in response to each of the subsequent one of the instructions 160. As previously described, the patient support apparatus 30 further comprises the control system 100 configured to control the operational functions of the patient support apparatus 30. The control system 100, in response to the user performing the user-performed actions, controls the operational functions. In the present example, the control system 100 controls the patient turning device 74 to independently inflate the elongate bladders to raise one side or both sides of the patient.

Figure 11:
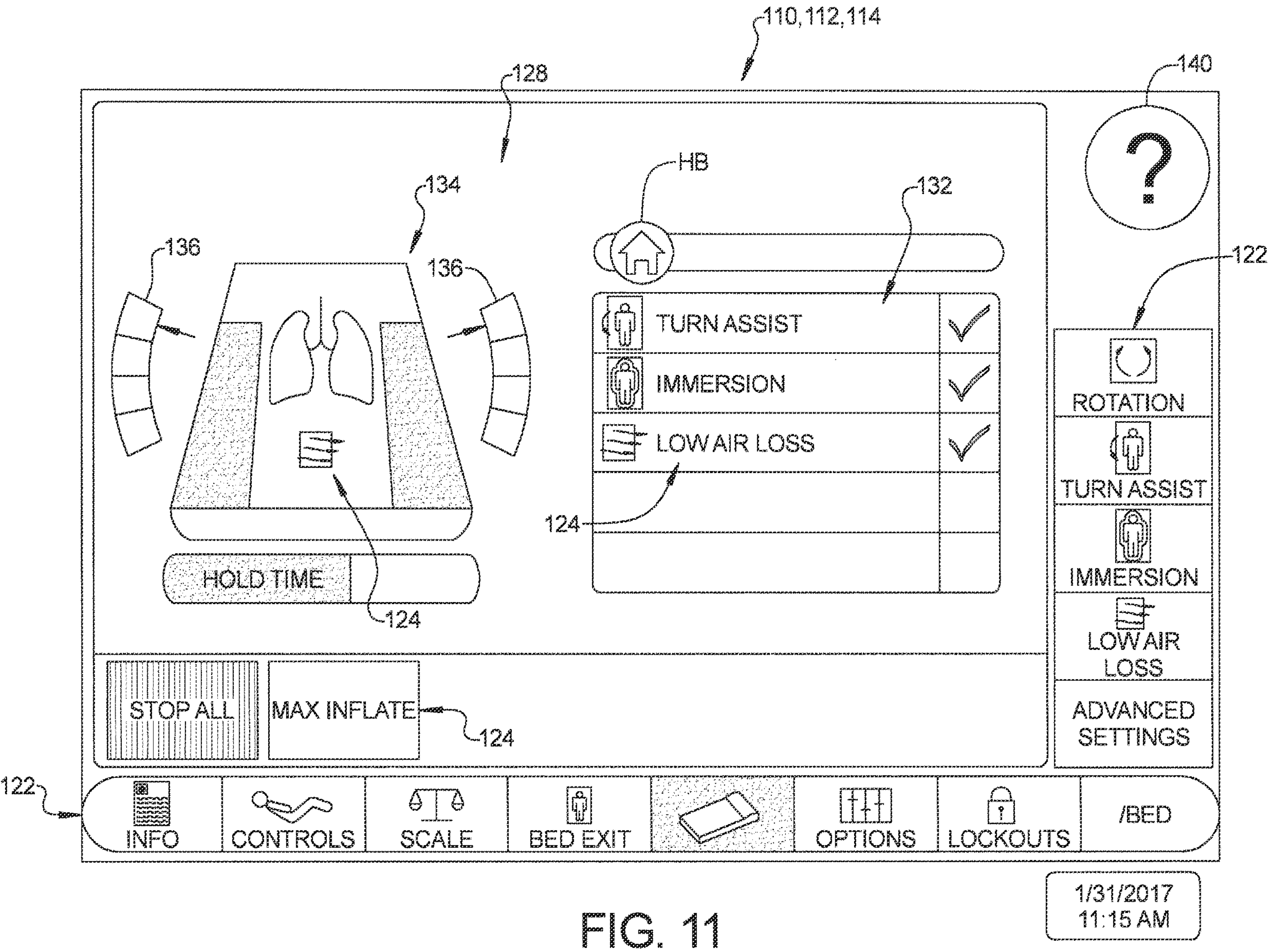
FIG. 11 is the touchscreen display of FIG. 4 displaying the user menu of FIG. 4 with a working area of the user menu updated in response to the user-performed actions.

Once the final user-performed action is completed such that the desired operational function of the patient support apparatus 30 is performed, the software application may return the user to the home menu or a previous user menu 130. FIG. 11 shows the previous user menu 130 including information reflective of the "Turn Assist" operational feature being in an active state. The selected operations list 132 of the working area 128 comprises text listing the "Turn Assist" as well as the checkmark indicative of being in the active state. As the most recently selected operational feature of the patient support apparatus 30, the text is positioned in a first position atop the selected operations list 132. The text may further comprise indicia 124 such that the text (and/or the checkmark) may be selected by the user with the user interface to selectively toggle the patient turning device 74 between the active and inactive states. Further, the operations graphic 134 has been updated to include shaded portions of the representation of the patient support apparatus 30 indicative of the elongated bladders adjacent the patient being inflated. Other ways of highlighting the elongated bladders such as by changing their color, brightness, etc. are also contemplated. The operations graphic 134 may also be dynamic and represent inflation/deflation of the elongated bladders. The arrows adjacent the arcuate gradients 136 now indicate the level of patient turning, which typically corresponds to the user input provided to the user interface 110 during the guidance protocol or during the navigation protocol.

It is to be understood that the operation described above is but one non-exhaustive example. A user may receive troubleshooting for any operational feature of the patient support apparatus 30 controllable from the user interface 110. For example, the guidance protocol facilitates control of the immersion device 72 or the low air loss device 94. For another example, the guidance protocol facilitates ordering replacement parts for the patient support apparatus 30 with the user interface 110.

In some cases, the user experiencing difficulty navigating the user menus 130 may be unaware of the advanced guidance and troubleshooting capabilities of the patient support system 28. The user may be unaware of or failed to notice the virtual help button 140. The patient support system 28 further provides predicative troubleshooting to initiate the troubleshooting capabilities without being requested by the user. In other words, the controller 102 of the patient support system 28 is configured to determine if the user is experiencing difficulty navigating the user menus 130 to control the operational functions of the patient support apparatus 30. In a preferred embodiment, the controller 102 is configured to initiate the guidance protocol based on an uncorrelated sequence of inputs from the user to the user interface 110. As described above, controlling operational functions of the patient support apparatus 30 often requires a sequence of user-performed actions. The sequence of user-performed actions often comprise successive inputs to the user interface 110 to navigate the user menus 130 comprising the home menu and the submenus 152. When the inputs are advancing the user towards controlling the desired operational feature(s), the inputs are considered to be correlated. With the user menus 130 of increased complexity (e.g., relative to those shown in FIGS. 4-9), there may be a plurality of "paths" that the user could take with some of the paths deviating from or unrelated to controlling the desired operational feature. In instances where the user provides inputs that are, for example, associated with different operational functions of the patient support apparatus 30, the inputs are considered to be uncorrelated. The controller 102 is configured to analyze the inputs to determine their correlation, or lack thereof, and determine whether the extent of the lack of correlation requires intervention through troubleshooting with the guidance protocol.

For purposes of the embodiments with predictive troubleshooting, the user-performed actions are described as "selections." Typically, the selections occur by actuating indicia 124 on the touchscreen display 114. The selections may comprise an initial selection, intermediate selections, and a final selection. The initial selection is associated with the home menu or other user menu 130 and, as described herein, generally directs the user to one of the submenus 152 associated with the initial selection (of indicia 124, 125, 126). The final selection is the actuation of the indicia 124, 125, 126 generally immediately prior to the desired operational feature moving to the active state or being made operational. In one example, the final selection causes the control system 100 to control one or more of the operational devices 70-92. In the earlier described example, the final selection was actuation of the play button PB (see FIG. 10), after which the control system 100 performed the action without further input from the user. The intermediate selections may be defined as any actuation of indicia 124, 125, 126 other than the initial selection and the final selection. Typically, the intermediate selections comprise actuation of indicia 124 of the working area 128 of the submenus 152 as the user navigates the user menus 130 to the final selection.

In some embodiments, the user may be prompted for troubleshooting assistance should the number of intermediate selections exceed a predetermined number. In one embodiment, the final selection is not considered in determining whether to prompt the user for troubleshooting assistance, since the final selection causes the desired action. In other words, if the user is making the final selection, it is unlikely the user is having difficulty navigating the user menus 130, otherwise he or she would not make the final selection (but rather continue navigating the submenus 152). It is to be understood that the final selection may be considered in determining whether the number of selections exceed the predetermined number such that the user is prompted for troubleshooting assistance.

The predetermined number may be based on any number of factors and/or metrics. In one example, empirical data may show that control of the operational functions of the patient support apparatus 30 averages three selections, excluding the initial and final selections. The predetermined number may be set at seven selections such that if the user makes seven or more intermediate selections, the information output device 112 provides a prompt to the user inquiring whether troubleshooting assistance is desired. In other words, the predetermined number could be, for example, the average number of a correlated sequence of inputs required to control the operational functions. Any number of selections exceeding the predetermined number is considered to be uncorrelated such that the user is "lost" within the submenus 152 of the software application. Often, the predetermined number may be sufficiently above the average such that a buffer is provided to avoid prompting the user too often, perhaps unwarrantedly, which may cause annoyance.

In another exemplary embodiment, the initial selection may be probative as to whether the intermediate selections comprise an uncorrelated sequence of inputs. In such an embodiment, it is assumed that the initial selection on the home menu was proper and the user is experiencing difficulty navigating the submenus 152. For example, to control the immersion device 72, it is unlikely the user would actuate the indicia 126 on the user menu 130 for "Turn Assist." Subsequently, the intermediate selections are analyzed quantitatively and qualitatively relative to the initial selection. Should, for example, the user make several selections in the submenus 152 associated with the patient turning device 74, but the initial selection was the indicia 126 on the home menu for "Immersion," the information output device 112 provides a prompt to the user inquiring whether troubleshooting assistance is desired. A database, algorithms, AI, and the like, may compile the relationships between the operational functions of the patient support apparatus 30 based on user inputs over time, and the predetermined number of intermediate selections before prompting may be adjusted accordingly. For example, a lower predetermined number of intermediate selections may be required between an initial selection directed to the immersion device 72 and intermediate selections involving submenus 152 directed to the patient raising device 78 than between an initial selection directed to the immersion device 72 and intermediate selections involving submenus 152 directed to low air loss device 94 (i.e., the immersion device 72 and the low air loss device 94 are related in many ways).

In some embodiments, actuating the "Back" button BB (see FIGS. 8-10) is excluded from the determination whether the number of intermediate selections exceeds the predetermined number. In some respects, the user actuating the button BB shows certain competencies with navigation of the user menus 130 of the software application, even if the button BB does not necessarily advance the user towards the final selection. In certain embodiments, the user is not precluded from actuating the button BB, but further actuation of the button BB a certain additional number of times may begin to toll the intermediate selections. Additionally, the controller may determine that troubleshooting assistance is required if the button BB is actuated more than a predetermined number of times within a predetermined time period, an indication that the user may be having difficulty with navigation. In other embodiments, actuation of the "Back" button BB is counted towards whether the number of intermediate selections exceeds the predetermined number.

The prompt for troubleshooting assistance may be provided with the information output device 112 in manners previously described and reasonably related thereto. For example, the prompt may comprise a pop-up window on the touchscreen display 114, or an audible question or instruction to the user. The user may elect to accept or forego proceeding with the troubleshooting request. Should the user elect to proceed, the user is further prompted to provide the troubleshooting request in the manners previously described. Subsequently, the guidance protocol is determined and executed.

In another exemplary embodiment, the determination of whether to prompt for troubleshooting assistance is based on analyzing the correlation between the known selections required for controlling a particular operational function and those selections made by the user. The guidance protocol, as mentioned, comprises the user-performed actions to be performed by the user in response to the instructions provided to the user. The navigation protocol may be the user-performed actions performed by the user without the instructions being provided to the user. In other words, the navigation protocol may be the guidance protocol if the user did not require troubleshooting. Consequently, in at least certain embodiments, the selections for controlling a particular operational function may be the same for the navigation protocol and its corresponding guidance protocol. As the user makes the initial selection and subsequent intermediate selections, an algorithm may be implemented to determine to which guidance protocol most closely matches the navigation protocol being enacted by the user. If, for example, the user has made a correlated sequence of three selections directed to controlling the operational function of the immersion device 72, the controller 102 determines and stores this information in non-transitory memory 131 in communication with the controller 102. Should the user subsequently deviate from the navigation protocol in an atypical manner, the software application may present the user with the prompt requesting troubleshooting assistance. An atypical manner would include deviating from the navigation protocol within the submenus 152. It may also be considered atypical to actuate the "home" button HB or the "back" buttons BB. In other embodiments, it would not be desirable to prompt the user for troubleshooting assistance after the user opts to merely return to the home menu or previous submenu 152, as the user should be able to freely navigate the software application to a reasonable extent. Yet, as the user makes multiple selections that evidence an intention of a certain course of action, it may be beneficial to prompt the user for troubleshooting assistance after the user deviates from completing the course of action in an atypical manner. AI and algorithms may be developed and implemented to learn and discern patterns of the user selections throughout the software application so as to optimize the timing and manner of the prompt for troubleshooting assistance.

In the above embodiments, regardless of whether the troubleshooting assistance is initiated by the system or by the user actuating the virtual help button 140, the controller 102 is configured to determine the guidance protocol based on the troubleshooting request from the user provided to the user interface 110. For example, as mentioned, the controller 102 determines the troubleshooting request, and consequently the guidance protocol, based on the input signals. Additionally or alternatively, the guidance protocol of the patient support system 28 is determined based on the input signals comprising the uncorrelated sequence of inputs to the user interface 110. Stated differently, the patient support system 28 utilizes predictive troubleshooting to determine what the user is attempting to accomplish without the user providing the troubleshooting request to the user interface 110. This may be in addition to the controller 102 being configured to automatically initiate the guidance protocol and/or prompt troubleshooting assistance based on the uncorrelated sequence of inputs to the user interface 110.

Determining the guidance protocol based on the uncorrelated sequence of inputs to the user interface 110 presents unique challenges beyond prompting for troubleshooting assistance. The present disclosure contemplates several methods for determining the guidance protocol, some of which are described below, and should be considered non-limiting examples. In one embodiment, each indicia 124, 125, 126 for the home menu and each of the submenus 152 are predefined as associated with one or more of the operational functions. In some respects, the predefined associations are inherent, as selecting one of the indicia 124, 125, 126 results in a consequent response from software application (e.g., directed to a submenu 152, etc.). The response from the software application moves the user towards an end result whether desired or not. These predefined associations are stored in the non-transitory memory 131 in, for example, a database format. A point value may be provided for each predefined association that is based on the nexus or relationship between the indicia 124, 125, 126 and the operational functions. For example, the indicia 126 of "Turn Assist" (see FIGS. 4-9) may have a point value of five for the patient turning device 74, and a point value of zero for the lift device 78; i.e., the indicia 126 of "Turn Assist" is more closely related to controlling the patient turning device 74, than the lift device 78. In certain embodiments, the initial selection may be weighted more heavily and assigned a greater point value relative to the intermediate selections, presupposing that the user at least initially selected the appropriate indicia 124, 125, 126 on one of the user menus 130. Further, the present disclosure contemplates the initial and intermediate selections may be associated with more than one of the operational functions, and the point values for each may be the same or different. For example, indicia 124 directed to controlling immersion may also be associated with low air loss device 94, since both operational devices 72, 94 are related in many respects (i.e. alleviating pressure on the mattress 40).

The user makes the initial selection on the home menu or the intermediate selection(s) on the submenus 152. As the user navigates the home menu or other user menu 130 and the submenus 152, the point values may be assigned and summed for each operational function. In other words, for each selection from the user to the user interface 110, the controller 102 assigns and sums the point values for each operational function of the patient support apparatus 30 based on its predefined association.

Based on the summed point values for each operational function, the controller 102 determines which of operational function the user is intending to operate. For example, following the troubleshooting request from the user, the information output device 112 may provide the user with one or more of the operational features having the highest point total(s). In other words, the higher the point total indicates the selections made by the user to that point have been most relevant to the certain operational functions. For example, the initial selection is the indicia 126 of "Immersion" on the user menu 130 of FIG. 4. After two intermediate selections in the subsequent submenus 152, the user makes a faulty intermediate selection that results in a submenu 152 directed to controlling the patient turning device 74. The user makes one additional faulty intermediate selection before actuating the virtual help button 140 for troubleshooting or before being prompted for troubleshooting assistance. Because the initial selection and the two intermediate selections were directed to controlling the immersion device 72, that particular operational function has a higher point total than the operational function directed to the patient turning device 74. In response, the information output device 112 may provide, visually and/or audibly, "Are you trying to operate the Immersion Device? Would you like assistance?" The user may provide input agreeing to further assistance if desired.

The information output device 112, for example, may provide two or more "suggested" operations from which the user may select. Due to the relatedness between, for example, the immersion device 72 and the low air loss device 94, operational function of the low air loss device 94 may also have a higher point total than the operational function of the patient turning device 74. A pop-up menu may be displayed on the information output device 112 titled "Would you like assistance?" with indicia 124 representative of the immersion device 72 and the low air loss device 94, perhaps among others. The predictive guidance and troubleshooting described throughout the present disclosure advantageously facilitates improved patient care and an improved user experience. The user menus 130 provide a well-organized, aesthetically appealing user experience. The indicia 124, 125, 126 may be actuated on the touchscreen display 114, and portions of the working area 128 including the selected operations list 132 and the operations graphic 134 also comprise selectable features that are intuitive for the user.

The patient support system 28 may further comprise a remote assistance system 170 remote from the patient support apparatus 30. Referring to FIG. 2, the remote assistance system 170 is in communication with the controller 102 and configured to transmit instruction signals to the controller 102 to provide the instructions 160 to the user with the information output device 112. Whereas the previously described embodiments utilize the software application stored on the non-transitory memory 131 or remote from the patient support apparatus 28 (e.g., via local area network), the remote assistance system 170 is configured to facilitate live support. The live support may comprise voice conferencing between a remote representative of the remote assistance system 170 and the user. The voice conferencing is facilitated with the information output device 112 and the user interface 110. The live support may also comprise videoconferencing between the remote representative of the remote assistance system 170 and the user. The videoconferencing is facilitated with the information output device 112 and the user interface 110. The live support may also comprise text messaging between the remote representative of the remote assistance system 170 and the user. The text messaging is facilitated with the information output device 112 and the user interface 110.

Figure 12:
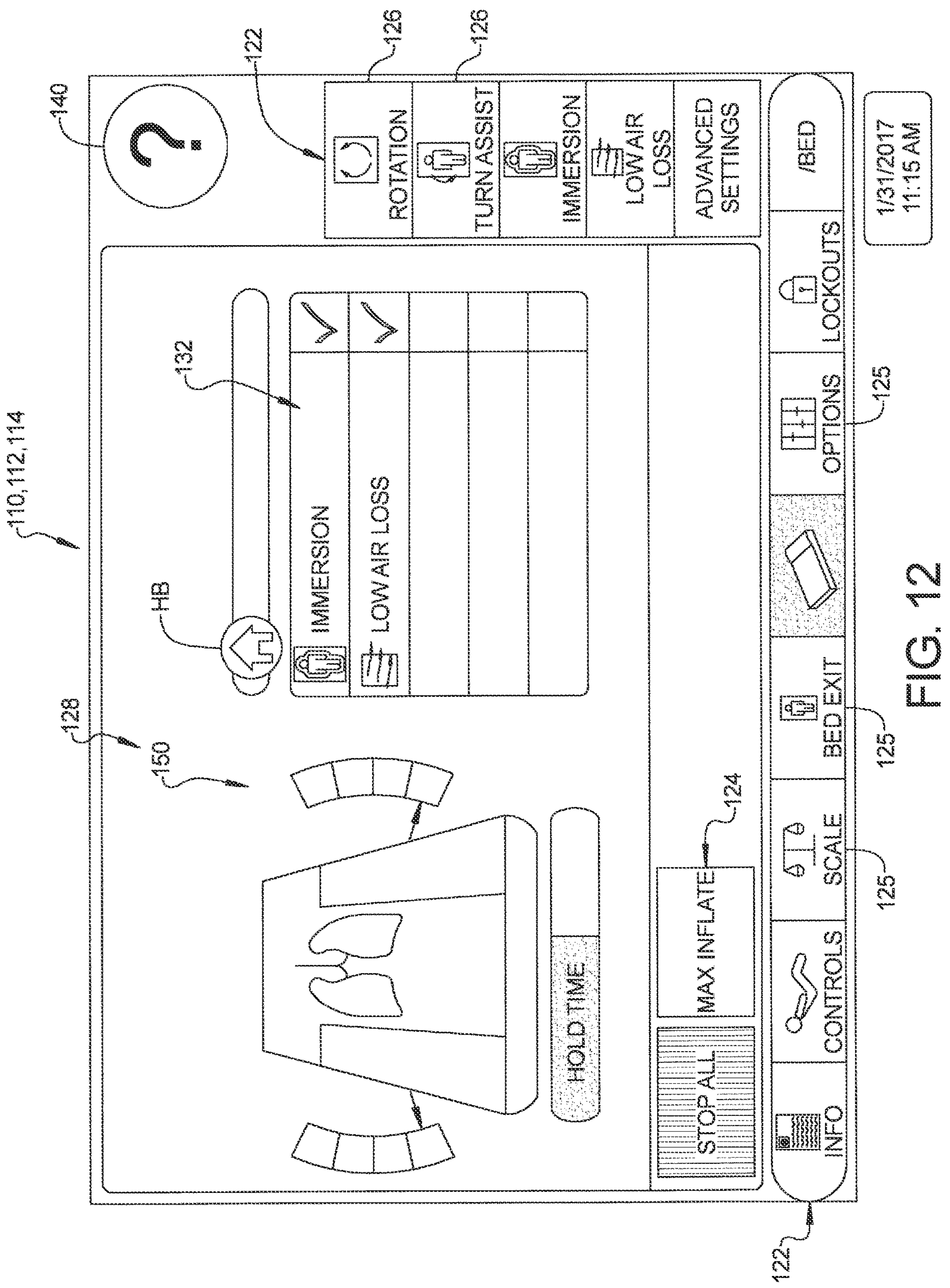
FIG. 12 is the touchscreen display of FIG. 4 displaying a user menu.
Figure 13:
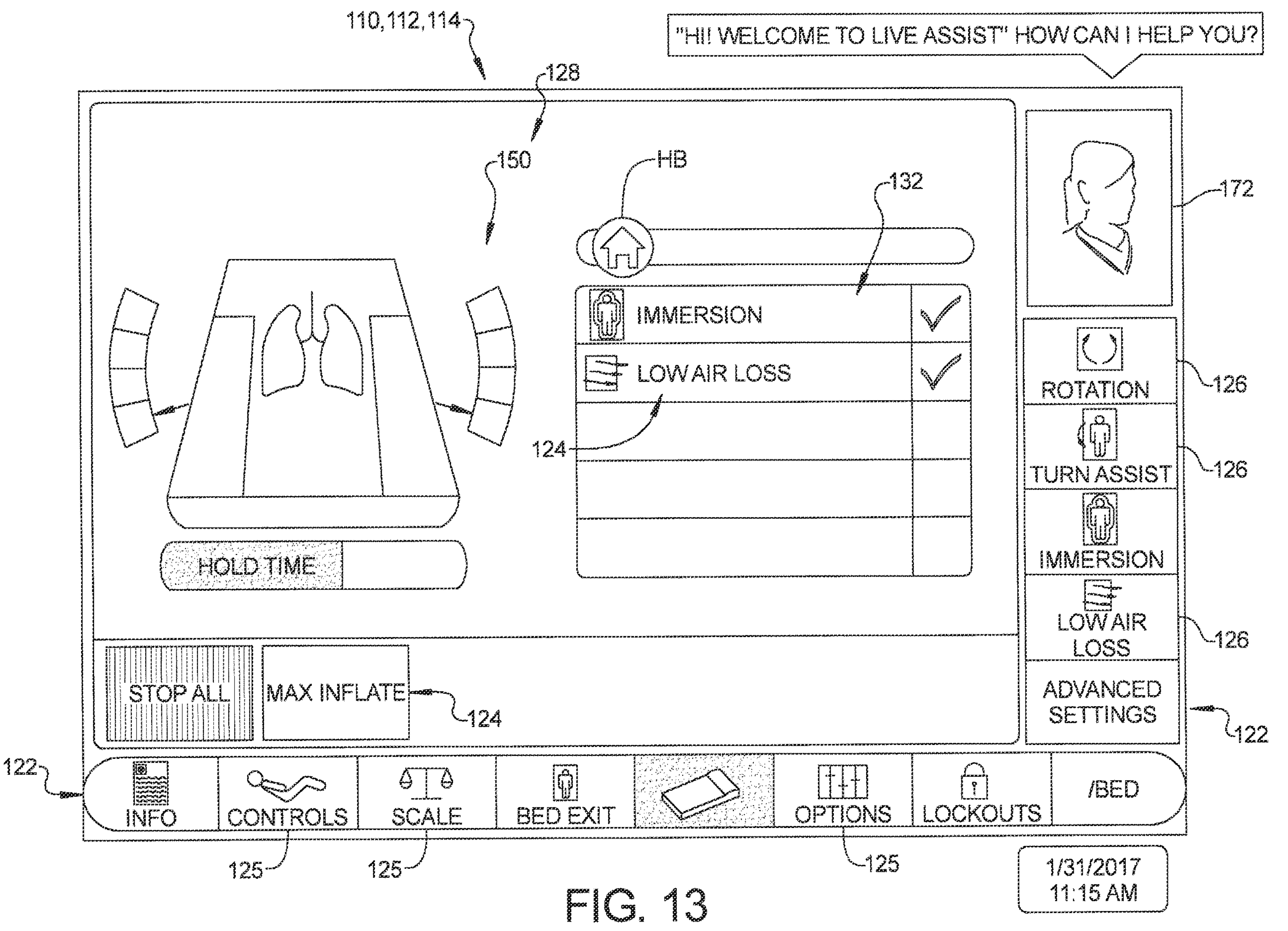
FIG. 13 is the touchscreen display of FIG. 4 displaying the user menu of FIG. 12 with a remote assistance system providing live support via voice conferencing or videoconferencing.

Referring to FIGS. 12 and 13, the working area 128 of the user menu 130 is the same as that shown in FIG. 4. FIG. 12 shows the virtual help button 140 positioned at the upper-right corner of the user menu 130. The user actuates the virtual help button 140 with the user interface 110. In response, the image or feed 172 of the remote representative of the remote assistance system 170 is displayed on the user menu 130, as shown in FIG. 13. The image or feed 172 is positioned in the taskbar 122, but any suitable size and arrangement is contemplated. In one embodiment, a pop-up window may be provided with the image or feed 172 of the remote representative disposed therein.

The remote representative is a human at a location remote from the patient support apparatus 30. Often, the remote representative is stationed at a call center configured to field technical support requests. In one embodiment, the image or feed 172 is a static picture, perhaps a stock photograph, and the live support comprises voice conferencing akin to a telephone call. In another embodiment, the image or feed 172 is a video feed, and the live support comprises the videoconference. The videoconference may be one-way (i.e., the user sees and hears the remote representative, and the remote representative only hears the user) or two-way (i.e., the remote representative and the user see and hear one another). A video camera may be coupled to the patient support apparatus 30 in a suitable manner to facilitate the videoconferencing.

The incoming text messages displayed on the information output device 112 may be submitted by the remote representative at a location remote from the patient support apparatus 30. A virtual keyboard comprising alphanumeric keys may be provided on the touchscreen display 114 comprising the user interface 110 to permit the user to prepare and send outgoing text messages to the remote representative.

For the voice conferencing, the videoconferencing, and the text messaging, the remote representative provides the guidance protocol comprising the instructions 160 to the user with the information output device 112. The instructions are provided at least audibly with the information output device 112 with speakers as the remote representative assists the user through the guidance protocol. In certain embodiments, the remote representative may provide visual instructions to the user with the information output device 112 comprising the touchscreen display 114. In one example, the remote representative may visually emphasize the indicia 124, 125, 126 in a manner previously described (see FIGS. 7-10), with the visual emphasis correlating the indicia 124, 125, 126 to what is being explained verbally by the remote representative. The arrangement facilitates improved troubleshooting with the remote representative escorting the user through the guidance protocol. In another example, the remote representative may be able to perform the user-performed action on behalf of the user should the user be unable to do so for whatever reason. Suitable safeguards are incorporated to ensure the remote representative is unable to perform operational functions of the patient support apparatus 30 that may be deleterious to the user's well-being (e.g., the remote representative may be prevented from moving the patient support surface 42). Any suitable systems and methods of voice and videoconferencing may be employed and integrated into the patient support apparatus 30.

Figure 14:
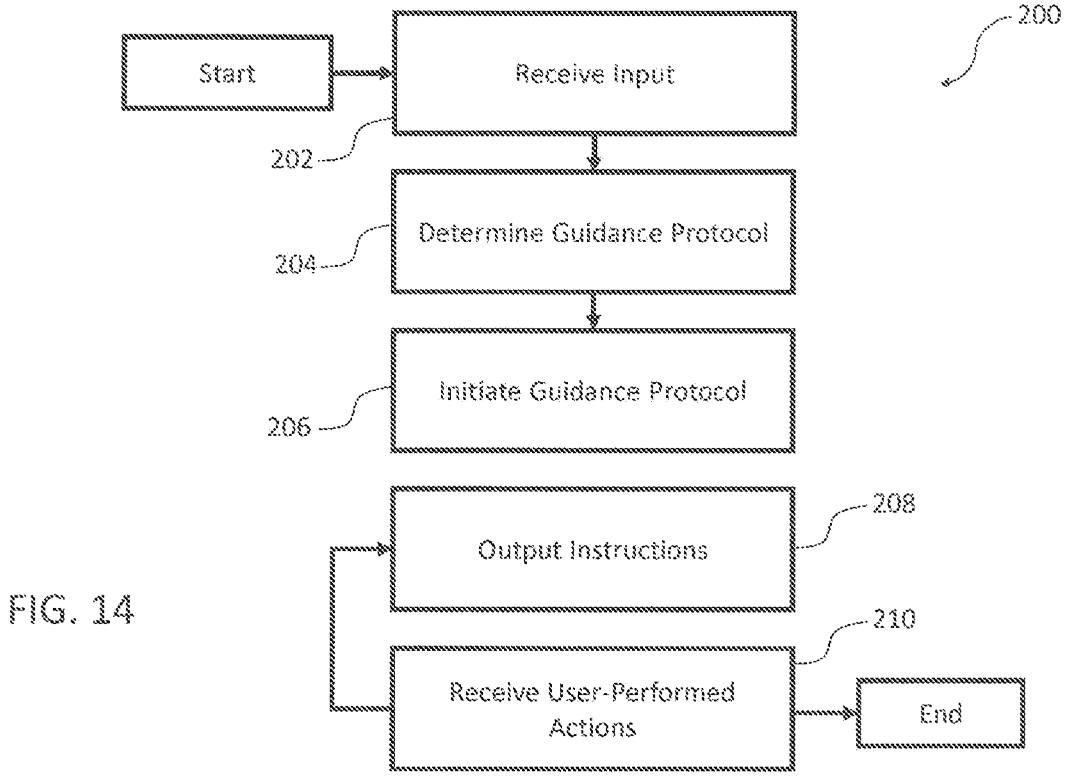
FIG. 14 is a schematic diagram detailing exemplary operation of the patient support system in accordance with certain embodiments of the present disclosure.

Exemplary methods of providing guidance to the user for the patient support system 28 are also provided. In certain embodiments, the patient support system 28 comprises the patient support apparatus 30, a user interface 110 configured to receive inputs from the user, and the information output device 112 configured to provide instructions to the user. One exemplary method 200 is shown in FIG. 14. Inputs are received from the user with the user interface 110 (step 202). In one example, indicia 124, 125, 126 may be visually displayed on the information output device 112, and the inputs may comprise the user selecting the indicia 124, 125, 126 with the user interface 110.

A guidance protocol is determined based on the inputs (step 204). The guidance protocol comprises steps of instruction 160 to be provided to the user on the information output device 112. The guidance protocol is initiated (step 206), and the instructions are outputted with the information output device 112 (step 208). For example, a first of the steps of instruction 160 is outputted with the information output device 112. User-performed actions are received with the user interface 110 in response to the steps of instruction 160 (step 210). For example, a first of the user-performed actions is received with the user interface 110 in response to the first step. The steps of outputting instructions and receiving user-performed actions may continue iteratively. For example, a second of the steps of instruction is outputted with the information output device 112 after the first user-performed action. The outputting of the first or second of the steps of instruction 160 may comprises visually emphasizing one of the indicia 124, 125, 126 on the information output device. The steps 208 and 210 may continue until completion of the guidance protocol, after which the method 200 ends.

In certain embodiments, the inputs may further comprise a first input and a second input. A correlation between the first input and the second input may be determined. The guidance protocol may be determined (step 204) based the determined correlation between the first input and the second input. The determined correlation may comprise an uncorrelated sequence of inputs. In some aspects, the guidance protocol may be initiated (step 206) based on the determined correlation comprises an uncorrelated sequence of inputs. More particularly, the guidance protocol may be initiated (step 206) once it is determined, by the controller 102, that the sequence of inputs from the user is uncorrelated as previously described. In other aspects, the guidance protocol is initiated (step 206) in response to a troubleshooting request from the user to the user interface 110.

It may be determined with the controller 102 whether the first step provided to the user is performed by the user with the first-user performed action. If the first-user performed action performed by the user is not the first step provided to the user, the first step may be again provided to the user with the information output device 110, or a third of the steps of instruction may be provided or outputted (step 208) with the information output device 112 with the third of the steps being different than the first or second steps of instruction 160.

A remote assistance system 170 may be provided and configured to facilitate live support with a representative over the network. The remote assistance system 170 may be in communication with the user interface 110 and the information output device 112 over a network, and comprise a representative remote from the patient support apparatus 30. The remote assistance system 170 is accessed over the network to request the guidance protocol. The steps of instruction are received from the remote assistance system 170 to be provided to the user with the information output device 112. The remote assistance system 170 may determine the guidance protocol. Accessing the remote assistance system 170 may comprise voice or videoconferencing with a representative on the information output device 112.

Figure 15:
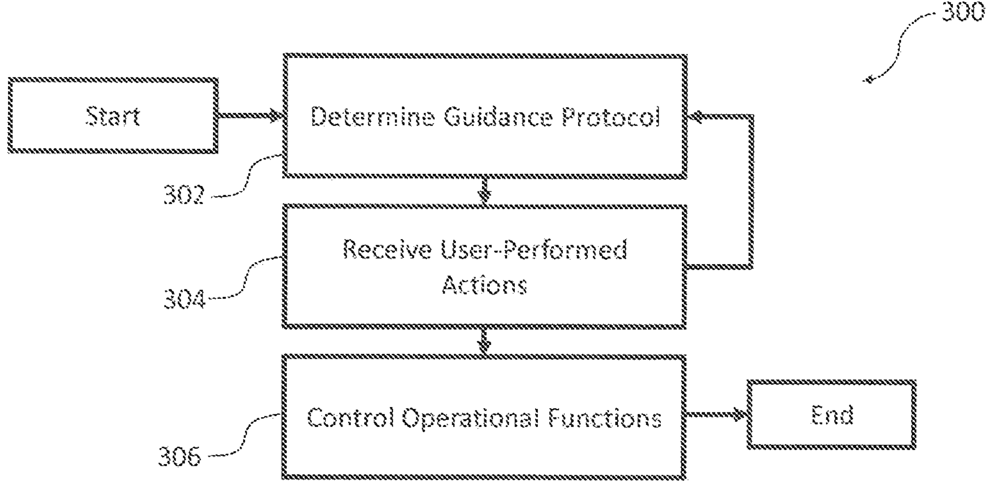
FIG. 15 is a schematic diagram detailing exemplary operation of the patient support system in accordance with certain embodiments of the present disclosure.

Referring to FIG. 15, another exemplary method 300 is shown the patient support system 28 comprises the control system 100 configured to control operational functions of the patient support apparatus 30. The method 300 comprises the step of providing the guidance protocol to the user with the information output device 112 (step 302). The guidance protocol may a plurality of steps each comprising one or more instructions 160. User-performed actions are received with the user interface 110 in response to the instructions 160 (step 304). More specifically, at each of the plurality of steps, an input signal is received with the user interface 110 and comprising a user-performed action in response to the provided instructions 160. The steps of outputting instructions 160 and receiving user-performed actions may continue iteratively until completion of the guidance protocol. At least one of the user-performed actions is configured to control operational functions of the patient support apparatus 30. The control system 100 controls the operational functions of the patient support apparatus 30 based on the at least one of the user-performed actions (step 306). The method 300 ends.

In some embodiments, indicia 124, 125, 126 may be visually displayed on the information output device 112 with the indicia 124, 125, 126 representative of the operational functions of the patient support apparatus 30. Provided the one or more instructions to the user comprises visually emphasizing the indicia 124, 125, 126 on the information output device.

As noted above, the subject patent application is related to U.S. Provisional Patent Application No. 62/525,363 filed on Jun. 27, 2017. In addition, the subject patent application is also related to: U.S. Provisional Patent Application No. 62/525,353 filed on Jun. 27, 2017 and its corresponding Non-Provisional patent application Ser. No. 16/020,068 filed on Jun. 27, 2018, now U.S. Pat. No. 11,337,872; U.S. Provisional Patent Application No. 62/525,359 filed on Jun. 27, 2017 and its corresponding Non-Provisional patent application Ser. No. 16/020,052 filed on Jun. 27, 2018, now U.S. Pat. No. 11,382,812; U.S. Provisional Patent Application No. 62/525,368 filed on Jun. 27, 2017 and its corresponding Non-Provisional patent application Ser. No. 16/019,973 filed on Jun. 27, 2018, now U.S. Pat. No. 11,096,850; U.S. Provisional Patent Application No. 62/525,373 filed on Jun. 27, 2017 and its corresponding Non-Provisional patent application Ser. No. 16/020,003 filed on Jun. 27, 2018, now U.S. Pat. No. 11,202,729; and U.S. Provisional Patent Application No. 62/525,377 filed on Jun. 27, 2017 and its corresponding Non-Provisional patent application Ser. No. 16/019,986 filed on Jun. 27, 2018, now U.S. Pat. No. 10,811,136. The disclosures of each of the above-identified Provisional Patent Applications and corresponding Non-Provisional Patent Applications are each hereby incorporated by reference in their entirety.

It will be further appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A patient support system comprising:

a patient support apparatus comprising a patient support surface and one or more powered operational devices configured to perform one or more operational functions for adjusting the patient support apparatus to at least partially move a patient relative to a floor surface;

a user interface configured to receive input from a user;

a display configured to provide instructions to the user;

a controller in communication with the user interface and the display, the controller being configured to:

present to the user, sequentially on the display, a plurality of steps of a guidance protocol to effect operation of the one or more powered operational devices, each of the plurality of steps comprising one or more of the instructions, at each of the plurality of steps, while a current step is visually emphasized on the display, receive an input signal comprising a user-performed action in response to the one or more of the instructions with at least one of the user-performed actions corresponding to a selection of a desired operational function of the one or more powered operational devices, and advance the guidance protocol to a next step and transmit a control signal to control at least one of the powered operational devices to perform the desired operational function in response to receiving the input signal at each of the plurality of steps until completion of the guidance protocol; and a remote assistance system remote from the patient support apparatus and in communication with the controller, the remote assistance system configured to transmit instruction signals to the controller to provide the instructions to the user with the display, wherein the remote assistance system is configured to facilitate live support comprising voice conferencing between a remote representative of the remote assistance system and the user with the display and the user interface.

2. The patient support system of claim 1, wherein the user interface and the display comprises a touchscreen display configured to output indicia selectable by the user with the user interface such that selection of the indicia comprises the user performing the user-performed actions.

3. The patient support system of claim 2, wherein the controller being configured to provide the instructions to the user on the touchscreen display comprises the controller visually emphasizing on the touchscreen display at least one of the indicia.

4. The patient support system of claim 2, wherein the touchscreen display is coupled to the patient support apparatus.

5. The patient support system of claim 2, wherein the touchscreen display is associated with a mobile device remote from the patient support apparatus.

6. The patient support system of claim 1, wherein the controller is further configured to provide a second of the instructions to the user with the display based on the input signal generated in response to the user performing a first of the user-performed actions.

7. The patient support system of claim 1, wherein the live support further comprises videoconferencing between the remote representative of the remote assistance system and the user with the display and the user interface.

8. The patient support system of claim 1, wherein the remote assistance system is configured to facilitate support comprising text messaging between a remote representative of the remote assistance system and the user with the display.

9. The patient support system of claim 1, wherein the user interface includes a device capable of receiving audible input and/or a device capable of providing audible output.

10. The patient support system of claim 1, wherein the one or more operational functions of the one or more powered operational devices include raising or lowering the patient support surface relative to a floor surface.

11. The patient support system of claim 1, wherein the one or more operational functions of the one or more powered operational devices include articulating one or more sections of the patient support apparatus.

12. The patient support system of claim 1, wherein the one or more operational functions of the one or more powered operational devices include controlling an inflation device to control immersion of the patient.

13. The patient support system of claim 1, wherein the one or more operational functions of the one or more powered operational devices include controlling a patient turning device to turn the patient.

14. The patient support system of claim 1, wherein the controller is further configured to determine the guidance protocol based on a troubleshooting request from the user provided to the user interface.

15. The patient support system of claim 14, wherein the guidance protocol is determined based on the input signal comprising an uncorrelated sequence of inputs to the user interface.

16. The patient support system of claim 1, wherein the controller is further configured to automatically initiate the guidance protocol based on the input signal comprising an uncorrelated sequence of inputs to the user interface.

17. The patient support system of claim 1, wherein, at one or more of the plurality of steps, the input signal is received with the user interface.

18. The patient support system of claim 1, wherein the user interface includes a voice integration system in communication with the controller; and wherein the controller is further configured to determine the guidance protocol based on voice input received from the user by the voice integration system.

19. A patient support system comprising:

a patient support apparatus comprising a patient support surface and one or more powered operational devices configured to perform one or more operational functions for adjusting the patient support apparatus to at least partially move a patient relative to a floor surface;

a user interface configured to receive input from a user;

a display configured to provide instructions to the user;

a controller in communication with the user interface and the display, the controller being configured to:

present to the user, sequentially on the display, a plurality of steps of a guidance protocol to effect operation of the one or more powered operational devices, each of the plurality of steps comprising one or more of the instructions, at each of the plurality of steps, while a current step is visually emphasized on the display, receive an input signal comprising a user-performed action in response to the one or more of the instructions with at least one of the user-performed actions corresponding to a selection of a desired operational function of the one or more powered operational devices, and advance the guidance protocol to a next step and transmit a control signal to control at least one of the powered operational devices to perform the desired operational function in response to receiving the input signal at each of the plurality of steps until completion of the guidance protocol; and a remote assistance system remote from the patient support apparatus and in communication with the controller, the remote assistance system configured to transmit instruction signals to the controller to provide the instructions to the user with the display, wherein the remote assistance system is configured to facilitate support comprising text messaging between a remote representative of the remote assistance system and the user with the display.

* * * * *